US011304659B2

United States Patent
Linder et al.

(10) Patent No.: US 11,304,659 B2
(45) Date of Patent: Apr. 19, 2022

(54) OPERATIVELY COUPLED DATA AND POWER TRANSFER DEVICE FOR MEDICAL GUIDEWIRES AND CATHETERS WITH SENSORS

(71) Applicant: XENTER, INC., Salt Lake City, UT (US)

(72) Inventors: Richard J. Linder, Sandy, UT (US); Edwin Meade Maynard, Salt Lake City, UT (US); Scott Kenneth Marland, Bountiful, UT (US); Cory Rex Estes, Mapleton, UT (US); Steven Matthew Quist, Salt Lake City, UT (US); Nathan J. Knighton, Syracuse, UT (US)

(73) Assignee: XENTER, INC., Salt Lake City, UT (US)

( * ) Notice: Subject to any disclaimer, the term of this patent is extended or adjusted under 35 U.S.C. 154(b) by 0 days.

(21) Appl. No.: 17/205,754

(22) Filed: Mar. 18, 2021

(65) Prior Publication Data

US 2021/0290100 A1 Sep. 23, 2021

Related U.S. Application Data

(60) Provisional application No. 63/044,960, filed on Jun. 26, 2020, provisional application No. 62/992,695, filed on Mar. 20, 2020.

(51) Int. Cl.
*A61B 5/00* (2006.01)
*A61B 5/0215* (2006.01)
(Continued)

(52) U.S. Cl.
CPC .......... *A61B 5/6852* (2013.01); *A61B 5/0002* (2013.01); *A61B 5/0215* (2013.01);
(Continued)

(58) Field of Classification Search
CPC ....... A61B 5/0215; A61B 1/05; A61B 5/6852; A61B 2562/222; A61B 2562/0247;
(Continued)

(56) References Cited

U.S. PATENT DOCUMENTS

| 4,595,012 A | * | 6/1986 | Webler | ........... | A61N 1/056 600/374 |
| 4,827,941 A | | 5/1989 | Taylor et al. | | |

(Continued)

FOREIGN PATENT DOCUMENTS

| CN | 103720463 A | 4/2014 |
| CN | 105919559 | 9/2016 |

(Continued)

OTHER PUBLICATIONS

Non-Final Rejection dated May 24, 2021 for U.S. Appl. No. 17/205,964.

(Continued)

*Primary Examiner* — Oommen Jacob
(74) *Attorney, Agent, or Firm* — Workman Nydegger

(57) ABSTRACT

A power and data coupling device for medical sensors comprises a first conductive surface integrated into a medical device and configured to couple via an electric field with a second conductive surface. The second conductive surface is translatable with respect to the first conductive surface. Additionally, the first conductive surface is connected to a power source for providing power, through the electric field, to the second conductive surface. The first conductive surface also radiates a time-varying electric field that is configured to convey power to the second conductive surface. Further, the first conductive surface is connected to a pick-up that is configured to receive signals from the second conductive surface.

26 Claims, 21 Drawing Sheets

(51) Int. Cl.
  *A61M 25/09* (2006.01)
  *H02J 50/90* (2016.01)
  *H02J 50/05* (2016.01)
  *H02J 50/40* (2016.01)
  *A61B 5/07* (2006.01)
  *A61B 1/05* (2006.01)
  *A61M 25/01* (2006.01)
  *A61B 8/12* (2006.01)

(52) U.S. Cl.
  CPC ............ *A61B 5/02158* (2013.01); *A61B 5/07* (2013.01); *A61B 5/6851* (2013.01); *A61M 25/09* (2013.01); *H02J 50/05* (2016.02); *H02J 50/402* (2020.01); *H02J 50/90* (2016.02); *A61B 1/05* (2013.01); *A61B 5/0059* (2013.01); *A61B 8/12* (2013.01); *A61B 2503/40* (2013.01); *A61B 2560/0214* (2013.01); *A61B 2560/0219* (2013.01); *A61B 2562/0247* (2013.01); *A61B 2562/06* (2013.01); *A61B 2562/222* (2013.01); *A61M 2025/0183* (2013.01)

(58) Field of Classification Search
  CPC ....... A61B 8/12; A61B 2562/06; A61B 5/287; A61B 5/02158; A61B 5/14546; A61B 2562/028; A61B 5/14539; A61B 5/14532; A61B 5/6851; A61M 25/09; A61M 2025/0183; A61N 1/00; A61N 1/056; A61N 1/36514; H02J 50/402
  See application file for complete search history.

(56) References Cited

U.S. PATENT DOCUMENTS

| | | | |
|---|---|---|---|
| 4,850,358 A | 7/1989 | Millar | |
| 4,917,104 A * | 4/1990 | Rebell | A61N 1/056 600/585 |
| 5,154,725 A | 10/1992 | Leopold | |
| 5,366,490 A | 11/1994 | Edwards et al. | |
| 5,368,035 A | 11/1994 | Hamm et al. | |
| 5,564,434 A | 10/1996 | Halperin et al. | |
| 5,651,767 A * | 7/1997 | Schulman | A61B 5/6865 600/372 |
| 5,790,081 A * | 8/1998 | Unwin | H01Q 9/145 343/745 |
| 5,814,089 A * | 9/1998 | Stokes | A61N 1/3787 607/32 |
| 5,860,974 A * | 1/1999 | Abele | A61B 8/4461 606/41 |
| 6,004,269 A * | 12/1999 | Crowley | A61B 8/4461 600/374 |
| 6,167,763 B1 | 1/2001 | Tenerz et al. | |
| 6,211,799 B1 * | 4/2001 | Post | H04L 12/10 341/33 |
| 6,245,020 B1 | 6/2001 | Moore et al. | |
| 6,248,076 B1 | 6/2001 | White et al. | |
| 6,479,785 B1 * | 11/2002 | Fugo | A61B 18/042 219/121.44 |
| 6,728,571 B1 | 4/2004 | Barbato | |
| 7,210,940 B2 | 5/2007 | Baily et al. | |
| 7,645,233 B2 | 1/2010 | Tulkki et al. | |
| 7,651,578 B2 | 1/2010 | Sharrow et al. | |
| 8,076,821 B2 | 12/2011 | Degertekin | |
| 8,277,386 B2 | 10/2012 | Ahmed et al. | |
| 8,362,673 B2 * | 1/2013 | Hsu | G02B 26/0833 310/300 |
| 8,473,067 B2 | 6/2013 | Hastings et al. | |
| 8,478,384 B2 | 7/2013 | Schmitt et al. | |
| 8,882,763 B2 * | 11/2014 | Stevenson | B82Y 30/00 606/41 |
| 9,106,270 B2 | 8/2015 | Puterbaugh et al. | |
| 9,192,306 B2 | 11/2015 | Chen | |
| 9,259,206 B2 | 2/2016 | Degertekin et al. | |
| 9,486,355 B2 | 11/2016 | Gustus et al. | |
| 9,667,323 B2 | 5/2017 | Habraken et al. | |
| 9,675,325 B2 | 6/2017 | Moore et al. | |
| 10,028,667 B2 | 7/2018 | Kishida et al. | |
| 10,080,872 B2 | 9/2018 | Webler | |
| 10,390,791 B2 | 8/2019 | Courtney et al. | |
| 10,391,292 B2 | 8/2019 | Sutton | |
| 10,418,755 B2 | 9/2019 | Kahlman | |
| 10,463,259 B2 | 11/2019 | Glover et al. | |
| 10,463,274 B2 | 11/2019 | Kassab et al. | |
| 10,531,841 B2 | 1/2020 | Merritt et al. | |
| 10,569,072 B2 | 2/2020 | Agrawal et al. | |
| 10,737,086 B2 | 8/2020 | Agrawal et al. | |
| 10,765,853 B2 | 9/2020 | Neff et al. | |
| 10,842,981 B2 | 11/2020 | Agrawal et al. | |
| 10,869,603 B2 | 12/2020 | Millett et al. | |
| 10,881,846 B2 | 1/2021 | Furnish et al. | |
| 2001/0001317 A1 | 5/2001 | Duerig et al. | |
| 2001/0029337 A1 * | 10/2001 | Pantages | A61B 8/12 600/463 |
| 2002/0013527 A1 | 1/2002 | Hoek et al. | |
| 2002/0151823 A1 | 10/2002 | Miyata et al. | |
| 2003/0083723 A1 * | 5/2003 | Wilkinson | A61N 1/056 607/122 |
| 2003/0120271 A1 | 6/2003 | Burnside et al. | |
| 2004/0064024 A1 * | 4/2004 | Sommer | A61N 1/057 600/374 |
| 2005/0143664 A1 | 6/2005 | Chen et al. | |
| 2006/0009817 A1 * | 1/2006 | Tulkki | A61B 5/6851 607/60 |
| 2006/0264925 A1 | 11/2006 | Sharareh et al. | |
| 2007/0118035 A1 * | 5/2007 | Secora | A61B 8/4461 600/466 |
| 2007/0191830 A1 | 8/2007 | Crompton et al. | |
| 2007/0255166 A1 * | 11/2007 | Carney | A61B 5/287 600/561 |
| 2008/0021336 A1 | 1/2008 | Dobak, III | |
| 2008/0177183 A1 * | 7/2008 | Courtney | A61B 1/00172 600/463 |
| 2009/0005859 A1 | 1/2009 | Keilman | |
| 2009/0110148 A1 | 4/2009 | Zhang et al. | |
| 2009/0156926 A1 | 6/2009 | Messerly et al. | |
| 2009/0171345 A1 | 7/2009 | Miller et al. | |
| 2009/0259772 A1 * | 10/2009 | Ketko | G06K 7/0021 710/13 |
| 2009/0284332 A1 * | 11/2009 | Moore | H01P 1/067 333/24 C |
| 2010/0087143 A1 | 4/2010 | Bonin | |
| 2010/0113939 A1 | 5/2010 | Mashimo et al. | |
| 2011/0190756 A1 * | 8/2011 | Venkatachalam | A61B 5/283 606/33 |
| 2011/0270369 A1 * | 11/2011 | Tekmen | A61N 1/0573 607/116 |
| 2012/0209061 A1 * | 8/2012 | Kato | A61B 1/05 600/103 |
| 2013/0064043 A1 | 3/2013 | Degertekin et al. | |
| 2013/0109980 A1 | 5/2013 | Teo | |
| 2013/0123638 A1 | 5/2013 | Tom et al. | |
| 2013/0204111 A1 | 8/2013 | Flanders | |
| 2013/0289424 A1 * | 10/2013 | Brockway | A61B 5/352 600/509 |
| 2013/0296692 A1 | 11/2013 | Vanney et al. | |
| 2014/0066705 A1 | 3/2014 | Robertson et al. | |
| 2014/0171788 A1 | 6/2014 | Stigall | |
| 2014/0180031 A1 | 6/2014 | Anderson | |
| 2014/0187978 A1 | 7/2014 | Millett et al. | |
| 2014/0236017 A1 | 8/2014 | Degertekin et al. | |
| 2014/0248801 A1 * | 9/2014 | Riezebos | H04B 5/0031 439/607.01 |
| 2014/0323860 A1 * | 10/2014 | Courtney | A61B 8/12 600/427 |
| 2015/0141854 A1 | 5/2015 | Eberle et al. | |
| 2015/0208901 A1 | 7/2015 | Gazdzinski | |
| 2015/0216403 A1 | 8/2015 | Whitmore, III | |
| 2015/0305708 A1 | 10/2015 | Stigall et al. | |
| 2015/0313478 A1 | 11/2015 | Veszelei et al. | |
| 2016/0249817 A1 | 9/2016 | Mazar et al. | |

(56) References Cited

U.S. PATENT DOCUMENTS

| | | |
|---|---|---|
| 2016/0310020 A1 | 10/2016 | Warnking et al. |
| 2017/0136496 A1* | 5/2017 | Jacobs .................. H01L 21/78 |
| 2017/0164867 A1 | 6/2017 | Kassab et al. |
| 2017/0164925 A1* | 6/2017 | Marshall ............... A61B 8/0891 |
| 2017/0215801 A1 | 8/2017 | Jung et al. |
| 2017/0266433 A1 | 9/2017 | Daniels et al. |
| 2018/0125365 A1 | 5/2018 | Hunter et al. |
| 2018/0262236 A1* | 9/2018 | Kahlman ............. H04B 5/0037 |
| 2018/0263515 A1 | 9/2018 | Raval |
| 2019/0053787 A1 | 2/2019 | Stigall et al. |
| 2019/0070402 A1 | 3/2019 | Isaacson |
| 2019/0133462 A1 | 5/2019 | Millett et al. |
| 2019/0167351 A1 | 6/2019 | Salazar et al. |
| 2019/0184159 A1 | 6/2019 | Yeh et al. |
| 2019/0290139 A1 | 9/2019 | Sio et al. |
| 2019/0358387 A1 | 11/2019 | Elbadry et al. |
| 2019/0380651 A1 | 12/2019 | Carreel et al. |
| 2020/0022587 A1 | 1/2020 | Glover et al. |
| 2020/0054227 A1 | 2/2020 | Van Rens |
| 2021/0290059 A1 | 9/2021 | Linder et al. |
| 2021/0290164 A1 | 9/2021 | Linder et al. |
| 2021/0290198 A1 | 9/2021 | Linder et al. |

FOREIGN PATENT DOCUMENTS

| | | | |
|---|---|---|---|
| DE | 19621003 | 1/1997 | |
| JP | 2016-518870 A | 3/2017 | |
| WO | 2018/017547 | 1/2018 | |
| WO | 2020/030776 A1 | 2/2020 | |
| WO | WO-2020030776 A1 * | 2/2020 | ........... A61B 5/0215 |

OTHER PUBLICATIONS

International Search Report and Written Opinion received for PCT Patent Application No. PCT/US21/023198, dated Jun. 14, 2021, 2 pages.

International Search Report and Written Opinion received for PCT Patent Application No. PCT/US21/23135, dated Jun. 8, 2021, 8 pages.

International Search Report and Written Opinion received for PCT Patent Application No. PCT/US21/23148, dated Jun. 4, 2021, 7 pages.

International Search Report and Written Opinion received for PCT Patent Application No. PCT/US21/23184, dated Jun. 7, 2021, 10 pages.

Aldaoud, et al. "A stent-based power and data link for sensing intravascular biological indicators." IEEE Sensors Letters 2.4 (2018): 1-4.

Degertekin FL, Guldiken RO, Karaman M. Annular-ring CMUT arrays for forward-looking IVUS: transducer characterization and imaging. IEEE Trans Ultrason Ferroelectr Freq Control. Feb. 2006;53(2):474-82.

E. F. Arkan and F. L. Degertekin, "Analysis and Design of High-Frequency 1-D CMUT Imaging Arrays in Noncollapsed Mode," in IEEE Transactions on Ultrasonics, Ferroelectrics, and Frequency Control, vol. 66, No. 2, pp. 382-393, Feb. 2019.

G. Jung, C. Tekes, A. Pirouz, F. L. Degertekin and M. Ghovanloo, "Supply-Doubled Pulse-Shaping High Voltage Pulser for CMUT Arrays," in IEEE Transactions on Circuits and Systems II: Express Briefs, vol. 65, No. 3, pp. 306-310, Mar. 2018.

Gurun G, Hasler P, Degertekin F. Front-end receiver electronics for high-frequency monolithic CMUT-on-CMOS imaging arrays. IEEE Transactions on Ultrasonics, Ferroelectrics, and Frequency Control. Aug. 2011;58(8):1658-1668.

Gurun G, Tekes C, Zahorian J, Xu T, Satir S, Karaman M, Hasler J, Degertekin FL. Single-chip CMUT-on-CMOS front-end system for real-time volumetric IVUS and ICE imaging. IEEE Trans Ultrason Ferroelectr Freq Control. Feb. 2014;61(2):239-50.

J. Lim, C. Tekes, E. F. Arkan, A. Rezvanitabar, F. L. Degertekin and M. Ghovanloo, "Highly Integrated Guidewire Ultrasound Imaging System-on-a-Chip," in IEEE Journal of Solid-State Circuits, vol. 55, No. 5, pp. 1310-1323, May 2020.

J. Lim, C. Tekes, F. L. Degertekin and M. Ghovanloo, "Towards a Reduced-Wire Interface for CMUT-Based Intravascular Ultrasound Imaging Systems," in IEEE Transactions on Biomedical Circuits and Systems, vol. 11, No. 2, pp. 400-410, Apr. 2017.

J. Zahorian et al., "Monolithic CMUT-on-CMOS Integration for Intravascular Ultrasound Applications," in IEEE Transactions on Ultrasonics, Ferroelectrics, and Frequency Control, vol. 58, No. 12, pp. 2659-2667, Dec. 2011.

Lim J, Arkan EF, Degertekin FL, Ghovanloo M. Toward a reduced-wire readout system for ultrasound imaging. Annu Int Conf IEEE Eng Med Biol Soc. 2014;2014:5080-4.

Lim J, Rezvanitabar A, Degertekin FL, Ghovanloo M. An Impulse Radio PWM-Based Wireless Data Acquisition Sensor Interface. IEEE Sens J. Jan. 15, 2019;19(2):603-614.

Lu, et al. "A review on the recent development of capacitive wireless power transfer technology." Energies 10.11 (2017): 1752.

Pirouz, A.; Degertekin, F.L. An Analysis Method for Capacitive Micromachined Ultrasound Transducer (CMUT) Energy Conversion during Large Signal Operation. Sensors 2019, 19, 876.

S. Satir and F. L. Degertekin, "A nonlinear lumped model for ultrasound systems using CMUT arrays," in IEEE Transactions on Ultrasonics, Ferroelectrics, and Frequency Control, vol. 62, No. 10, pp. 1865-1879, Oct. 2015.

S. Satir, J. Zahorian and F. L. Degertekin, "A large-signal model for CMUT arrays with arbitrary membrane geometry operating in non-collapsed mode," in IEEE Transactions on Ultrasonics, Ferroelectrics, and Frequency Control, vol. 60, No. 11, pp. 2426-2439, Nov. 2013.

Satir S, Degertekin FL. Phase and Amplitude Modulation Methods for Nonlinear Ultrasound Imaging With CMUTs. IEEE Trans Ultrason Ferroelectr Freq Control. Aug. 2016;63(8):1086-92.

Sharei, et al. "Data communication pathway for sensing guidewire at proximal side: A review." Journal of Medical Devices 11.2 (2017).

Tanase et al. "Multi-parameter sensor system with intravascular navigation for catheter/guide wire application", Sensors and Actuators A: Physical vols. 97-98, Apr. 1, 2002, pp. 116-124.

Tekes C, Zahorian J, Gurun G, et al. Volumetric imaging using single chip integrated CMUT-on-CMOS IVUS array. Annu Int Conf IEEE Eng Med Biol Soc. 2012;2012:3195-3198.

Final Office Action received for U.S. Appl. No. 17/205,854, dated Sep. 23, 2021, 14 pages.

* cited by examiner

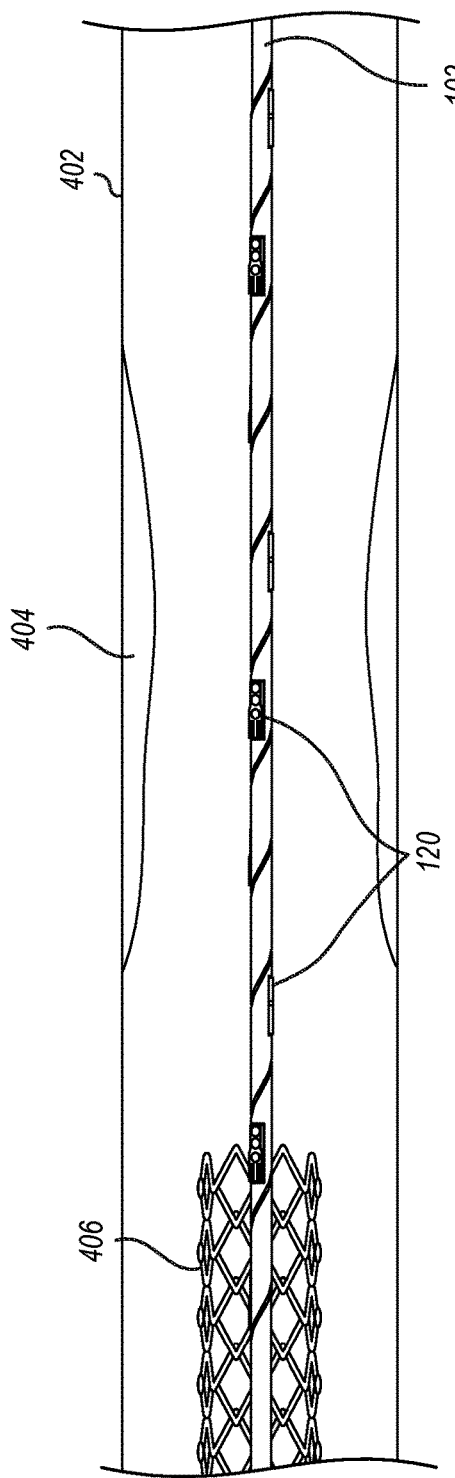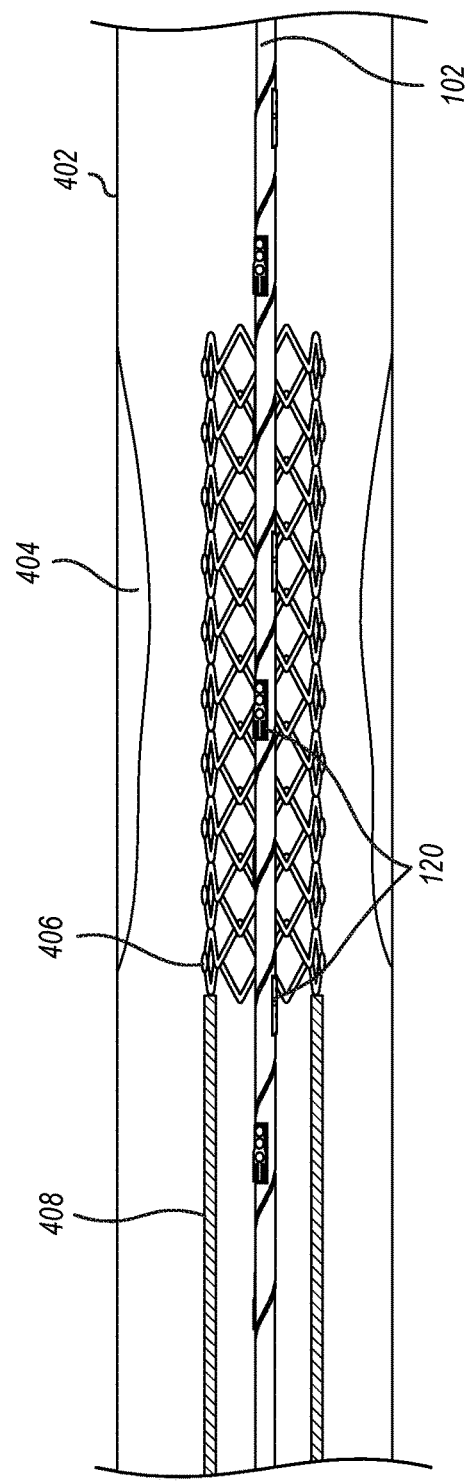

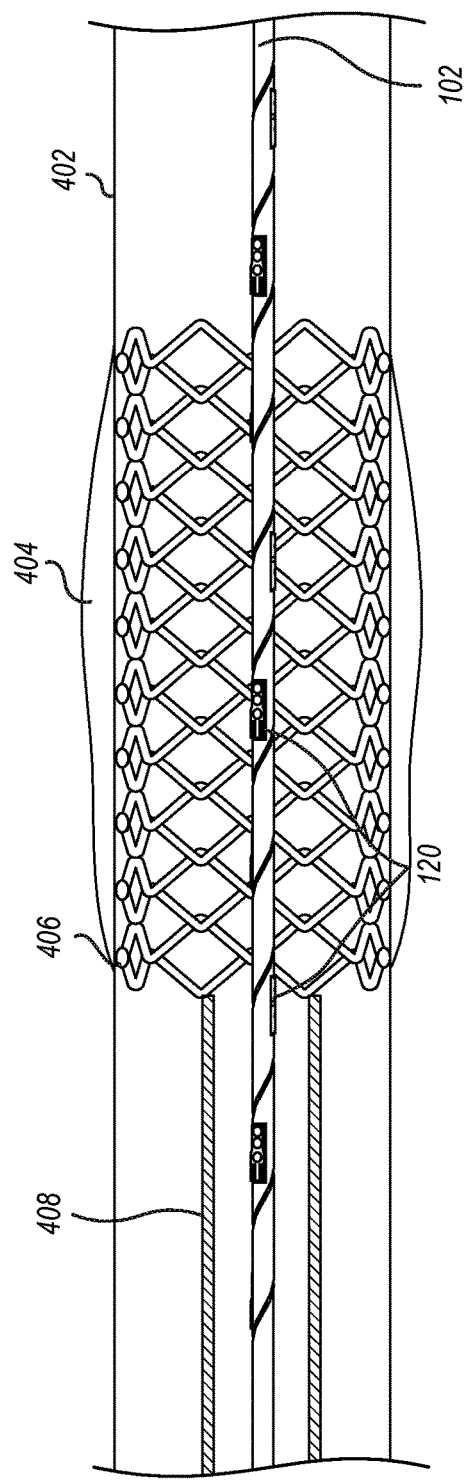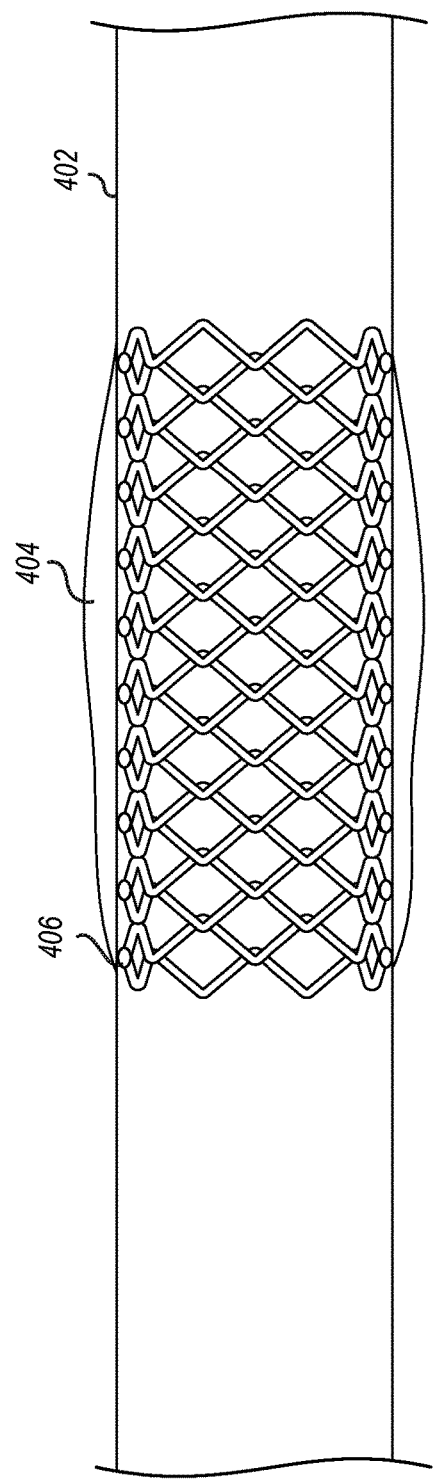

OPERATIVELY COUPLED DATA AND POWER TRANSFER DEVICE FOR MEDICAL GUIDEWIRES AND CATHETERS WITH SENSORS

CROSS-REFERENCE TO RELATED APPLICATIONS

This application claims priority to U.S. Provisional Patent Application Ser. No. 62/992,695, filed Mar. 20, 2020 and titled "CATHETER SYSTEM, DEVICE, AND METHOD THEREOF," and to U.S. Provisional Patent Application Ser. No. 63/044,960, filed Jun. 26, 2020 and titled "CATHETER AND GUIDEWIRE SYSTEMS WITH ENHANCED LOCATION AND CHARACTERIZATION FEATURES." The entire contents of each of the above applications is incorporated herein by reference in their entireties.

Additionally, the present application is related to U.S. patent application Ser. No. 17/205,614 filed Mar. 18, 2021 entitled "SIGNAL CONDUCTING DEVICE FOR CONCURRENT POWER AND DATA TRANSFER TO AND FROM UN-WIRED SENSORS ATTACHED TO A MEDICAL DEVICE", U.S. patent application Ser. No. 17/205,854 filed Mar. 18, 2021 entitled "CATHETER FOR IMAGING AND MEASUREMENT OF PRESSURE AND OTHER PHYSIOLOGICAL PARAMETERS", and U.S. patent application Ser. No. 17/205,964 filed Mar. 18, 2021 entitled "GUIDEWIRE FOR IMAGING AND MEASUREMENT OF PRESSURE AND OTHER PHYSIOLOGICAL PARAMETERS". The entire contents of each of the above applications is incorporated herein by reference in their entireties.

BACKGROUND

The present invention relates generally to medical devices, including intraluminal devices such as guidewires and catheters that include various sensors for simultaneous and/or continuous measuring of one or more physiological parameters.

Guidewire devices are often used to lead or guide catheters or other interventional devices to a targeted anatomical location within a patient's body. Typically, guidewires are passed into and through a patient's vasculature in order to reach the target location, which may be at or near the patient's heart or brain, for example. Radiographic imaging is typically utilized to assist in navigating a guidewire to the targeted location. Guidewires are available with various outer diameter sizes. Widely utilized sizes include 0.010, 0.014, 0.016, 0.018, 0.024, and 0.035 inches in diameter, for example, though they may also be smaller or larger in diameter.

In many instances, a guidewire is placed within the body during the interventional procedure where it can be used to guide multiple catheters or other interventional devices to the targeted anatomical location. Once in place, a catheter can be used to aspirate clots or other occlusions, or to deliver drugs, stents, embolic devices, radiopaque dyes, or other devices or substances for treating the patient.

These types of interventional devices can include sensors located at the distal portion in order to provide added functionality to the device. For example, intravascular ultrasound (IVUS) is an imaging technique that utilizes a catheter with an ultrasound imaging sensor attached to the distal portion. Ultrasound is utilized to image within targeted vasculature (typically the coronary arteries).

The use of such sensors introduces several challenges. In particular, the interventional devices involved have very limited space to work in, given the stringent dimensional constraints involved. Moreover, integrating the sensors with the interventional device in a way that maintains effective functionality can be challenging.

Another issue common to the field is proper localization and positioning of the distal portion of the device at the target location. If the device tip is improperly positioned during insertion, or if the tip migrates away from the desired position after insertion, various risks can arise. For catheter implementations, for example, improper positioning can lead to fluid infusions that can cause pain or injury to the patient, increased thrombosis rates, delays in therapy, device breakage or malfunction, delays due to device replacement, and additional costs associated with the device replacement and the additional time required by the attending physician and the medical center.

Further, conventional approaches to internal imaging and catheter localization require the injection of dye and/or the use of X-rays. Each of these can be harmful to the subject. In addition, such imaging radiation can be harmful to the physicians and staff exposed to the radiation.

The use of such interventional devices is also challenging due to the need to manage several long lengths of wires and other components, including guidewires, power cables, data wires, and the like. Care must be taken with respect to what is allowed in the sterile field and when it can be removed. Additional staff is often required simply to manage such wires and cables.

As such, there is an ongoing need for improved interventional devices that effectively integrate sensors, effectively manage power and data communication with the sensors, effectively communicate data off of the device for additional processing, and that enable more effective positioning of the medical device in the desired target position within the vasculature or other targeted anatomy.

SUMMARY

Disclosed embodiments include a power and data coupling device for medical sensors. The power and data coupling device may comprise a first conductive surface integrated into a medical device and configured to couple via an electric field with a second conductive surface. The second conductive surface may be translatable with respect to the first conductive surface. Additionally, the first conductive surface may be connected to a power source for providing power, through the electric field, to the second conductive surface. The first conductive surface may also radiate a time-varying electric field that is configured to convey power to the second conductive surface. Further, the first conductive surface may be connected to a pick-up that is configured to receive signals from the second conductive surface.

Additional disclosed embodiments include a method for providing power and data coupling to medical sensors. The method may comprise coupling, via a time-varying electric field, a first conductive surface integrated into a medical device with a second conductive surface. The first conductive surface may be connected to a power source for providing power to the second conductive surface. The first conductive surface may radiate a time-varying electric field that is configured to convey power to the second conductive surface. Additionally, the first conductive surface may be configured to receive signals from the second conductive surface. The method may further comprise translating the second conductive surface with respect to the first conductive surface. Additionally, the method may comprise isolating, with a signal processor, the signals. Further, the method may comprise transmitting, with a transmitter, the isolated signals to a computing device.

This Summary is provided to introduce a selection of concepts in a simplified form that are further described below in the Detailed Description. This Summary is not intended to identify key features or essential features of the claimed subject matter, nor is it intended to be used as an aid in determining the scope of the claimed subject matter.

Additional features and advantages will be set forth in the description which follows, and in part will be obvious from the description, or may be learned by the practice of the teachings herein. Features and advantages of the invention may be realized and obtained by means of the instruments and combinations particularly pointed out in the appended claims. Features of the present invention will become more fully apparent from the following description and appended claims, or may be learned by the practice of the invention as set forth hereinafter.

BRIEF DESCRIPTION OF THE DRAWINGS

Various objects, features, characteristics, and advantages of the invention will become apparent and more readily appreciated from the following description of the embodiments, taken in conjunction with the accompanying drawings and the appended claims, all of which form a part of this specification. In the Drawings, like reference numerals may be utilized to designate corresponding or similar parts in the various Figures, and the various elements depicted are not necessarily drawn to scale, wherein:

FIGS. 4A-4D illustrate an exemplary use of the guidewire system to effectively guide positioning and deployment of a stent at a targeted stenosis;

DETAILED DESCRIPTION

Overview of Intraluminal Systems

Figure 1:
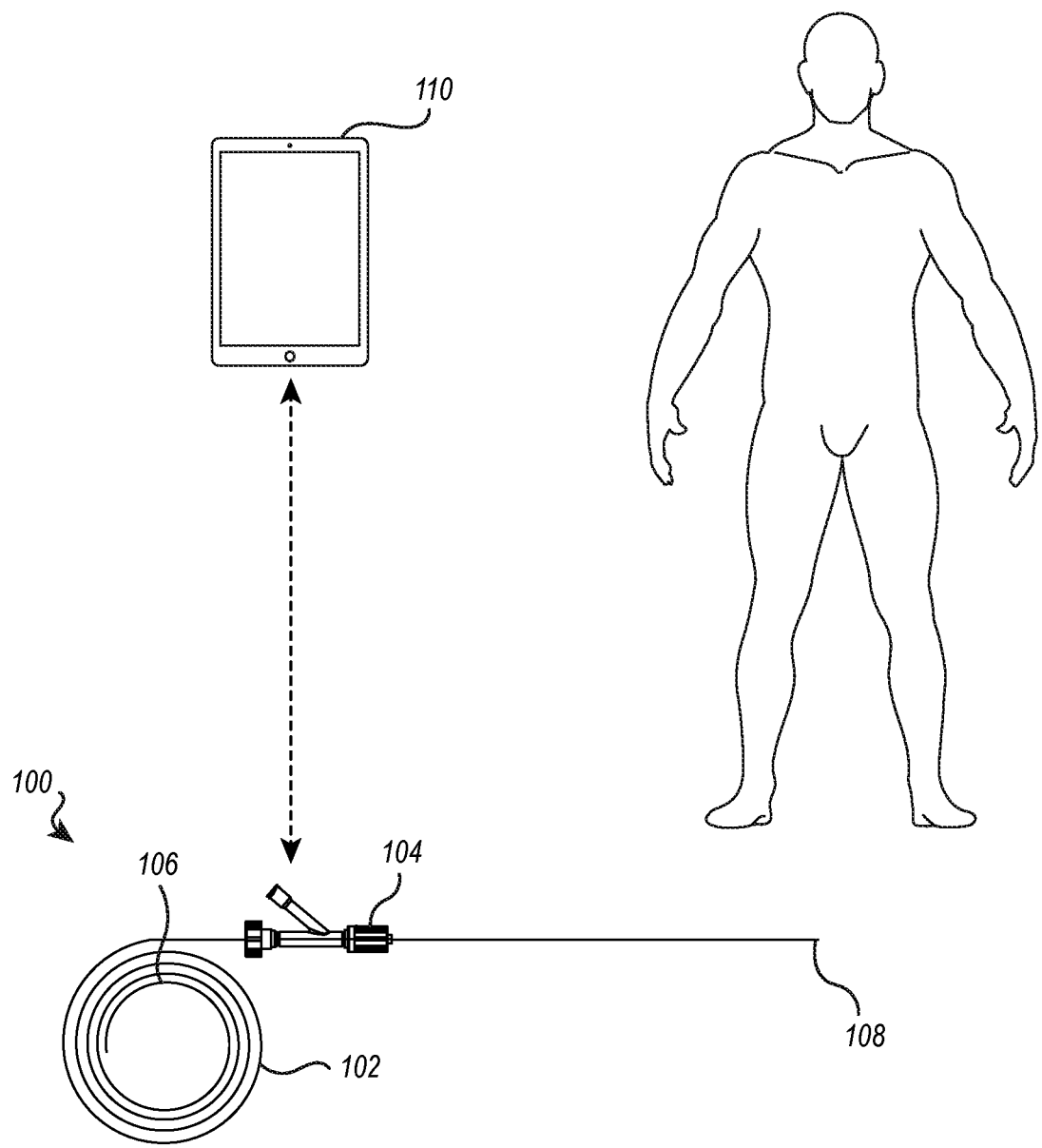
FIG. 1 illustrates a schematic overview of a guidewire system configured to provide one or more of the features described herein.

FIG. 1 illustrates a schematic overview of a guidewire system 100 that may incorporate one or more of the features described herein. The guidewire system 100 includes a wire 102 that is routable through a proximal device 104. The guidewire system 100 may sometimes be alternatively referred to herein as the "guidewire device. As used herein, the wire 102 may also be referred to as a type of elongated conductive member.

As used herein, the elongated conductive member comprises any conductive component that is longer than it is wide. For example, the elongated conductive member includes the wire 102. For the sake of example and explanation, the elongated conductive member may also be referred to as the wire 102; however, one will appreciate the wire 102 is a subset of possible elongated conductive members. For example, the elongated conductive member may also comprise a catheter.

The "wire" of the guidewire system 100 refers to the solid wire element that forms the backbone of the guidewire system 100. The term "wire", when used in the context of the guidewire system 100, is therefore intended to refer to a structure that has sufficient characteristics of torqueability, pushability, and stiffness/flexibility to be navigable within a body (e.g., capable of being positioned within an intraluminal space such as the vasculature). Such a "wire" element is sometimes referred to in the art as a "core", "core wire", or the like. This type of "wire" is therefore intended to be distinguished from smaller, less structured elements such as traces or leads that are capable of carrying an electrical signal but lack sufficient structure to be effectively navigated and positioned within the body to reach targeted anatomy. As an example, a "wire" suitable for use as part of the guidewire system 100 can have an average outside diameter of at least about 0.003 inches, or about 0.005 inches, or about 0.008 inches, or about 0.010 inches. In another example, a "wire" suitable for use as part of the guidewire system 100 can have yield strength above 10 ksi, or more preferably above 30 ksi, or more preferably above 50 ksi, or more preferably above 100 ksi, or more preferably above 150 ksi, or more preferably above 200 ksi, or more preferably above 250 ksi, such as 300 ksi. Additionally, or alternatively, the "wire" suitable for use as part of the guidewire system 100 can have a shear modulus above 6.7 msi, or more preferably above 8 msi, or more preferably above 10 msi, such as about 12 msi. Additionally, or alternatively, the "wire" suitable for use as part of the guidewire system 100 can have a modulus of elasticity of above 16 msi, or more preferably above 20 msi, or more preferably above 25 msi, such as about 30 msi.

The wire 102 of the guidewire system 100 is configured for insertion into the body of a subject. The subject is typically a human, but in other implementations may be a non-human mammal or even non-mammalian animal. Any suitable route of administration may be utilized, depending on particular preferences and/or application needs. Common routes include femoral, radial, and jugular, but the guidewire system 100 may utilized other access routes as needed.

Although many of the examples described herein relate to use of the guidewire system 100 or the catheter system 200 (see FIG. 2) in relation to intravascular procedures (e.g., cardiovascular or neurovascular), it will be understood that the described systems may be utilized in other medical applications as well. Other medical applications where the systems described herein may be utilized include, for example, applications involving access of the lymphatic, urinary/renal, gastrointestinal, reproductive, hepatic, or respiratory systems.

The proximal device 104 is shown here as a hemostatic valve, though in other embodiments the proximal device 104 may include additional or alternative forms. The proximal device 104 may also be referred to herein as the "power and data coupling device 104" or simply the "coupling device 104".

The wire 102 has a proximal portion 106 and a distal portion 108. The length of the wire 102 may vary according to particular application needs and targeted anatomical area. As an example, the wire 102 may have an overall length from proximal portion 106 to distal portion 108 of about 50 cm to about 350 cm, more commonly about 200 cm, depending on particular application needs and/or particular anatomical targets. The wire 102 may have a size such that the outer diameter (e.g., after application of other outer members) is about 0.008 inches to about 0.040 inches, though larger or smaller sizes may also be utilized depending on particular application needs. For example, particular embodiments may have outer diameter sizes corresponding to standard guidewire sizes such as 0.010 inches, 0.014 inches, 0.016 inches, 0.018 inches, 0.024 inches, 0.035 inches, 0.038 inches, or other such sizes common to guidewire devices. The wire 102 may be formed from stainless steel or other metal or alloy having appropriate mechanical properties. Additionally or alternatively, the wire 102 may be formed from an electrically conductive material of appropriate mechanical properties.

The coupling device 104 may also include or be associated with a transmitter to enable wireless communication between the guidewire system 100 and an external device 110 (or multiple such external devices). In alternative embodiments, the guidewire system 100 and external device 110 may be connected via a wired connection.

The external device 110 may be a hand-held device, such as a mobile phone, tablet, or lap-top computer. Although exemplary embodiments are described herein as using hand-held or mobile devices as the external devices 110, it will be understood that this is not necessary, and other embodiments may include other "non-mobile" devices such as a desktop computer, monitor, projector, or the like. In some embodiments, the external device 110 includes a mobile/hand-held device and additionally includes a desktop device or other non-mobile device. For example, a mobile device may be configured to receive transmitted data from the transmitter and function as a bridge by further sending the data to the non-mobile computer system. This may be useful in a situation where the physician would like the option of viewing data on a mobile device but may need to have the data additionally or alternatively passed or mirrored on a larger monitor such as when both hands are preoccupied (e.g., while handling the guidewire system 100).

The external device 110 of the guidewire system 100 may assist the physician in determining a position of the distal tip of the wire 102 within a vessel or other targeted anatomy of the human body. In this manner, the physician can appropriately position the wire 102 while also obtaining data of various parameters at the targeted anatomy so that the physician can better understand the relevant environment and make appropriate decisions while treating a patient.

The wireless system(s) may include, for example, a personal area network (PAN) (e.g., ultra-high frequency radio wave communication such as Bluetooth®, ZigBee®, BLE, NFC), a local area network (LAN) (e.g., WIFI), or a wide area network (WAN) (e.g., cellular network such as 3G, LTE, 5G). Wireless data transmission may additionally or alternatively include the use of light signals (infrared, visible radio, with or without the use of fiber optic lines), such as radiofrequency (RF) sensors, infrared signaling, or other means of wireless data transmission.

As used herein, "electrical signals" and "signals" both refer generally to any signal within a disclosed system, device, or method. Whereas, "sensor data signal," "sensor signal," or "data signal" refers to any signal that carries commands or information generated by a medical device, such as a medical sensor. In contrast, "power signal" or "energy signal" refers to any signal that provides power to a medical device, such as a sensor. In some cases, a "signal" may comprise both a data signal and a power signal.

Processing of sensor data signals may be fully or primarily carried out at the external device 110, or alternatively may be at least partially carried out at one or more other external devices communicatively connected to the external device 110, such as at a remote server or distributed network. Additionally or alternatively, sensor data signals may be processed at the coupling device 104, on the wire 102, or at some combination of devices within the guidewire system 100. Sensor data signals may include, for example, image data, location data, and/or various types of sensor data (as related to fluid flow, fluid pressure, presence/levels of various gases or biological components, temperature, other physical parameters, and the like).

As explained in greater detail below, one or more sensors may be coupled to the wire 102, and the one or more sensors can operate to send data signals through the wire 102 to the coupling device 104. Additionally, or alternatively, the coupling device 104 may operate to send power or signals to the one or more sensors.

Figure 2:
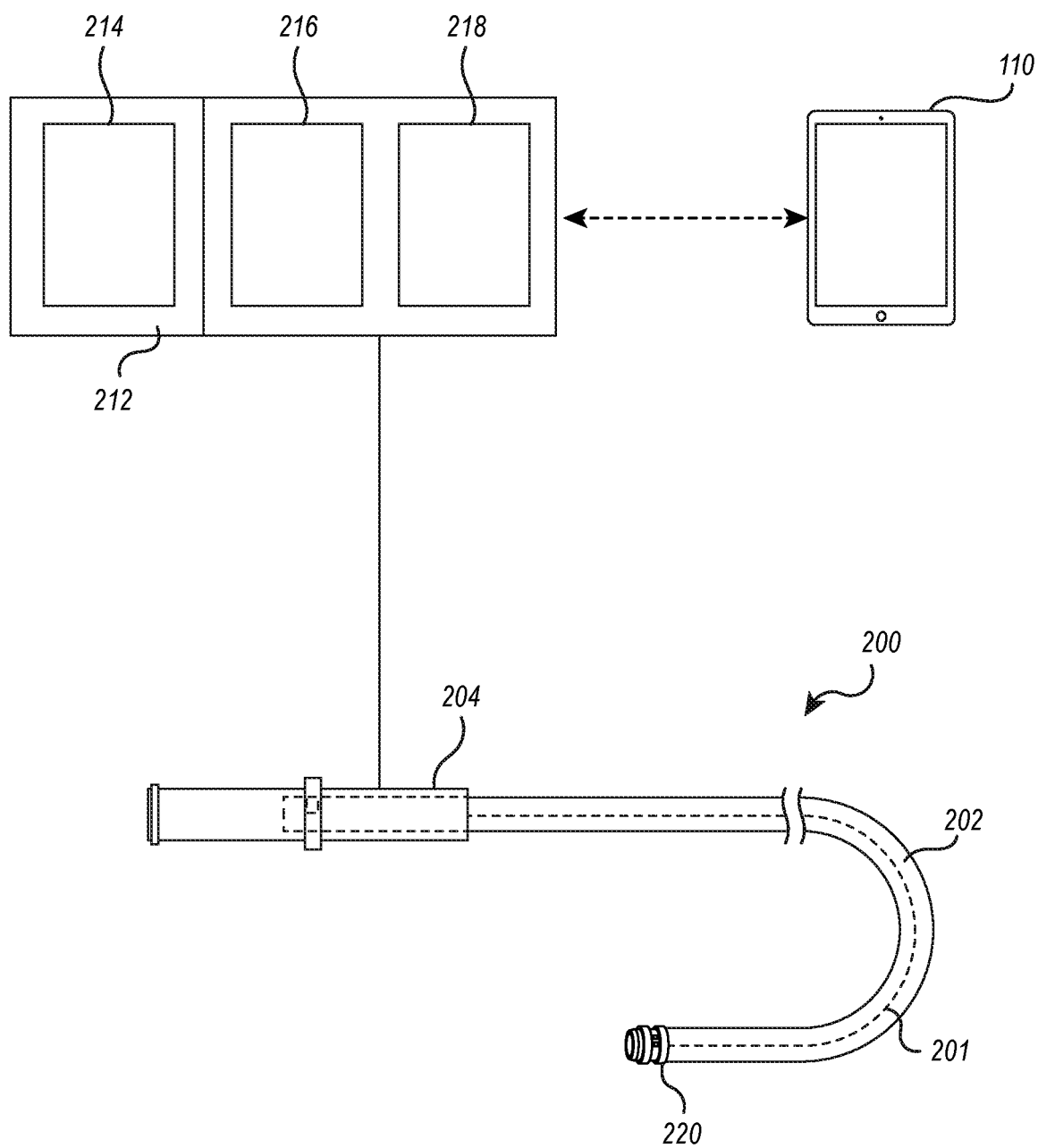
FIG. 2 illustrates a catheter system configured to provide one or more of the features described herein, showing components of a power and data transfer device and showing the that the coupling transfer device may be communicatively coupled to an external device.

FIG. 2 is an overview of a catheter system 200 that may incorporate one or more of the features described herein. The catheter system 200 may be similar to the guidewire system 100 in many respects, and the above description related to the guidewire system 100 is also applicable here except where differences are specified.

The catheter system 200 includes a catheter 202 and a proximal device 204 (which may also be referred to herein as "the power and data coupling device 204" or just "the coupling device 204"). The coupling device 204 includes a control unit 212 (shown enlarged and in schematic form) that includes a power source 214, data signal processor 216, and optionally a transmitter 218. The transmitter 218 enables wireless communication to the external device 110 (or multiple such devices) as described above with respect to FIG. 1. As used herein, the catheter 202 may also be referred to as a type of elongated conductive member.

The data signal processor 216 is configured to receive sensor data signals, sent through the catheter 202, from one or more sensors 220 associated with the catheter 202. The power source 214 is configured to transmit power through the catheter 202 to power the one or more sensors 220 and/or other components of the catheter 202. The power source 214 may include an on-board power source, such as a battery or battery pack, and/or may include a wired connection to an outside power source. The one or more sensors 220 may be located at any suitable position on the catheter 202 but will typically be disposed at the distal section of the catheter 202 expected to reach the targeted anatomy. Sensors 220 may be coupled to the catheter 202 by employing bonding, molding, co-extrusion, welding and/or gluing techniques, for example.

Power lines and/or data lines 201 extend along the length of the catheter 202 to the one or more sensors 220. As used herein, a "power line" and/or "data line" refer to any electrically conductive pathway (e.g., traces) within the medical device. Although multiple power and/or data lines 201 may be utilized, preferred embodiments are configured to send both power and data on a single line and/or manage sensor data signals from multiple sensors on a single line. This reduces the number of lines that must be routed through the structure of the catheter 202 and more effectively utilizes the limited space of the device, as well as reducing the complexity of the device and the associated risk of device failure.

The proximal device 204 may include one or more ports to facilitate the introduction of fluids (e.g., medications, nutrients) into the catheter 202. The catheter 202 may be sized and configured to be temporarily inserted in the body, permanently implanted in the body, or configured to deliver an implant in the body. In one embodiment, the catheter 202 is a peripherally inserted central catheter (PICC) line, typically placed in the arm or leg of the body to access the vascular system of the body. The catheter 202 may also be a central venous catheter, an IV catheter, coronary catheter, stent delivery catheter, balloon catheter, atherectomy type catheter, or IVUS catheter or other imaging catheter. The catheter 202 may be a single-lumen or multi-lumen catheter.

Figure 3A:
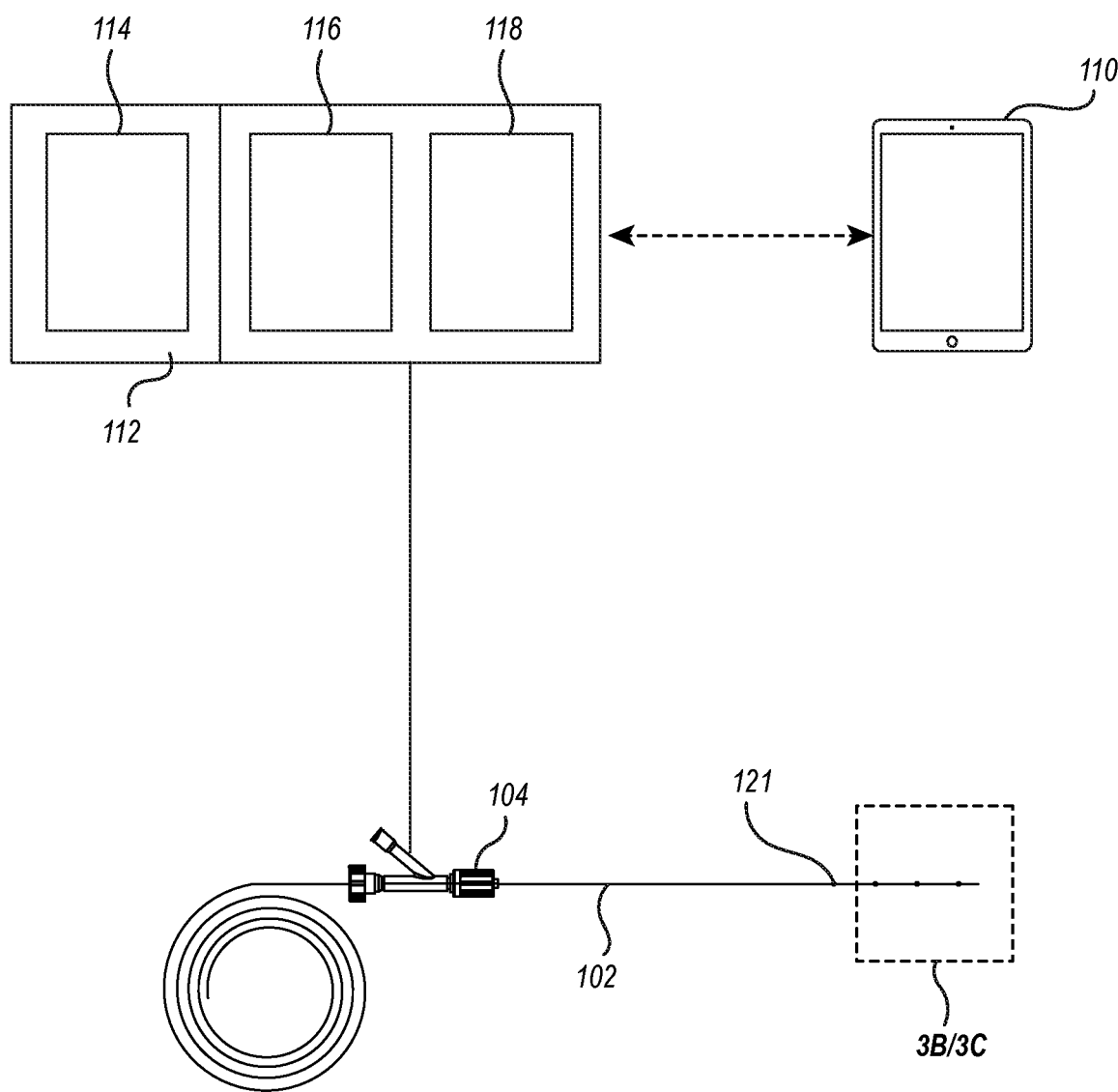
FIG. 3A illustrates a more detailed view of the guidewire system of FIG. 1, showing components of a power and data coupling device and showing that the coupling transfer device may be communicatively coupled to an external device.

FIG. 3A provides another view of the guidewire system 100 of FIG. 1. The guidewire system 100 shares certain features with the catheter system 200, and the description of common parts is therefore applicable to the guidewire system 100 as well. As shown, the guidewire system 100 includes a control unit 112 (shown enlarged and in schematic form) that includes a power source 114, data signal processor 116, and optionally a transmitter 118. The transmitter 118 enables wireless communication to the external device 110 (or multiple such devices) as described above.

The data signal processor 116 is configured to receive sensor data signals, sent through the wire 102, from one or more sensors 121 associated with the wire 102. The power source 114 is configured to transmit power through the wire 102 to power the one or more sensors 121 and/or other components of the wire 102. The power source 114 may include an on-board power source, such as a battery or battery pack, and/or may include a wired connection to an outside power source. The one or more sensors 121 may be located at any suitable position on the wire 102 but will typically be disposed at the distal section expected to reach the targeted anatomy. As used herein, the "distal section" or "distal portion" refers to the distal-most 30 cm of the device, the distal-most 20 cm of the device, the distal-most 15 cm of the device, the distal-most 10 cm of the device, or to a range using any two of the foregoing values as endpoints. In some embodiments, the "intermediate section" may be considered as roughly the middle third of the device, and the "proximal section" or "proximal portion" may be considered as roughly the proximal third of the device.

Unlike the catheter system 200, the guidewire system 100 is configured to send these power and data signals through the actual wire 102 itself. In some embodiments, multiple power and/or data signals (e.g., data signals from multiple sensors 121) can be sent through the wire 102 simultaneously. Power and/or data signals can also be sent in a "continuous" fashion. That is, the power and/or data signals can have a sufficiently high sampling rate such that the information is provided to the user within time frames that are practically "real-time". For most applications, this will include sampling rates of approximately 5 seconds or less, 3 seconds or less, 1 second or less, or sub-second sampling rates.

Using the wire 102 itself to send power and/or data signals through the device provides several benefits. For example, using the wire 102 to transmit these signals reduces or eliminates the need to run other connection lines along the wire 102 to connect the sensors 121 to the proximal portion and/or to deliver power to the sensors. Given the fact that guidewires inherently involve strict dimensional and performance (e.g., torqueability, bending, pushability, stiffness, etc.) limitations and have limited space to work in, the ability to reduce or eliminate extraneous components frees up limited space and allows greater design flexibility. Reducing or eliminating the use of additional connection lines also reduces the overall complexity of the device and thereby reduces the risk of component failure, leading to a more robustly functional device.

Additional Sensor Details

The one or more sensors 121 of the guidewire system 100 and/or the one or more sensors 121 of the catheter system 200 may include a pressure sensor, flow sensor, imaging sensor, or a component detection sensor, for example. A pressure sensor (or multiple pressure sensors) may be sized and configured to sense changes in pressure in the environment. A flow sensor (or multiple flow sensors) may be sized and configured to sense the fluid flow, such as velocity or other flow characteristics. A detection sensor (or multiple detection sensors) may detect a proximity or distance to one or more detection nodes positioned external relative to the body. An imaging sensor may gather various forms of imaging data.

The one or more sensors may additionally or alternatively be configured to sense the presence of substrates or measure physiological parameters in the targeted anatomical location (e.g., in the blood). Example biological components that may be detected/measured include sugar levels, pH levels, $CO_2$ levels ($CO_2$ partial pressure, bicarbonate levels), oxygen levels (oxygen partial pressure, oxygen saturation), temperature, and other such substrates and physiological parameters. The one or more sensors may be configured to sense the presence, absence, or levels of biological components such as, for example, immune system-related molecules (e.g., macrophages, lymphocytes, T cells, natural killer cells, monocytes, other white blood cells, etc.), inflammatory markers (e.g., C-reactive protein, procalcitonin, amyloid A, cytokines, alpha-1-acid glycoprotein, ceruloplasmin, hepcidin, haptoglobin, etc.), platelets, hemoglobin, ammonia, creatinine, bilirubin, homocysteine, albumin, lactate, pyruvate, ketone bodies, ion and/or nutrient levels (e.g., glucose, urea, chloride, sodium, potassium, calcium, iron/ferritin, copper, zinc, magnesium, vitamins, etc.), hormones (e.g., estradiol, follicle-stimulating hormone, aldosterone, progesterone, luteinizing hormone, testosterone, thyroxine, thyrotropin, parathyroid hormone, insulin, glucagon, cortisol, prolactin, etc.), enzymes (e.g., amylase, lactate dehydrogenase, lipase, creatine kinase), lipids (e.g., triglycerides, HDL cholesterol, LDL cholesterol), tumor markers (e.g., alpha fetoprotein, beta human chorionic gonadotrophin, carcinoembryonic antigen, prostate specific antigen, calcitonin), and/or toxins (e.g., lead, ethanol).

Unless stated otherwise, when reference is made to sensors (either generically or to a specific type of sensor) it should be understood to be inclusive of the supporting electronics as well. Supporting electronics may include, for example, power regulators, converters, signal amplifiers, processing components such as application-specified integrated circuits (ASICs), field-programmable gate arrays (FPGAs), and the like. The supporting electronics of the one or more sensors 121 are preferably positioned near the one or more sensors 121 themselves (e.g., at the distal section on a substrate). This was beneficially found to reduce signal drift as compared to placing the supporting electronics at the proximal sections of the device. Placing the supporting electronics (e.g., ASICs) on the distal portion near the sensors 121, and using the wire 102 itself as the means of transmitting data signals to the proximal end, provides effective signal transmission without the significant drift problems of other approaches.

Guidewire Sensor Arrangement & Distal Features

Figure 3B:
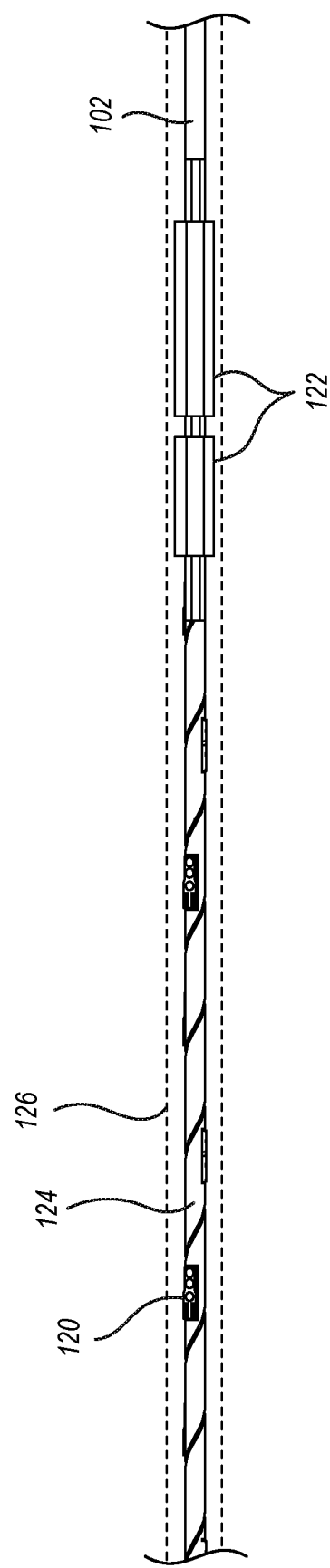
FIG. 3B is an expanded view of a distal section of the guidewire to better illustrate exemplary sensor arrangement on the guidewire.

FIG. 3B illustrates an expanded view of the distal section of the guidewire system 100 of FIG. 3A, showing various sensors arranged thereon. In this embodiment, the one or more sensors 121, 220 include multiple pressure sensors 120 and ultrasound sensors 122. These sensors are positioned on a substrate 124 and the substrate 124 is positioned on the wire 102 in a manner that places the sensors at their respective desired positions. The substrate 124 may be made of a somewhat flexible material (e.g., a suitable medical grade polymer) that allows wrapping, winding, or otherwise positioning the substrate 124 onto the wire 102. The substrate 124 also includes flexible circuitry such as trace lines and/or one or more conductive contacts to couple the sensors to the underlying wire 102. The substrate 124 can form a friction fit with the wire 102 and can additionally or alternatively be mechanically bonded to the wire 102.

Coupling the sensors to the substrate 124 and then placing the substrate 124 on the wire 102 provides several benefits. For example, the substrate 124 can be spread into what is essentially a 2-dimensional layout, which makes it much easier to appropriately position the sensors. The 2-dimensional substrate 124, with sensors coupled thereto, can then be placed on the 3-dimensional cylindrical shape of the wire 102 more readily than placing each sensor separately onto the wire 102. In particular, it is easier to ensure that the various sensors are appropriately positioned relative to one another on the substrate 124 and then to position the substrate 124 onto the wire 102 than to attempt to control relative spacing of each sensor on the 3-dimensional cylindrical shape of the wire 102. One will appreciate, however, that in at least one embodiment, the various sensors can be directly placed on the 3-dimensional wire 102 without the benefit of a 2-dimensional substrate 124. Alternatively, the various sensors can be placed on the substrate after the substrate has been applied to the 3-dimensional wire 102.

The illustrated embodiment also includes an outer member 126 (shown here with dashed lines) that can be positioned over the sensor-containing portion of the wire 102. The outer member 126 may be formed from a suitable medical grade polymer (e.g., polyethylene terephthalate (PET) or polyether block amide (PEBA)). The outer member 126 can function to further constrain and maintain position of the sensors and/or to smooth over the outer surface for a more uniform outer diameter. The outer member 126 may be applied by shrink-fitting a tube in place, by dip coating, and/or through other manufacturing methods known in the art. A hydrophilic coating may also be added to the outer surface of the device.

Figure 3C:
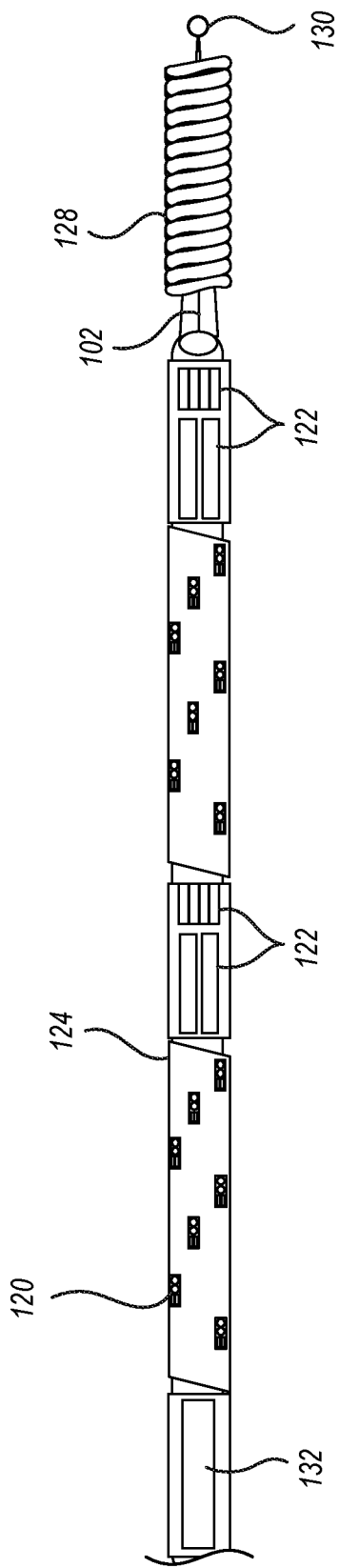
FIG. 3C is a schematic view of a distal section of the guidewire to illustrate additional distal components and features of the device.

FIG. 3C illustrates another, schematic view of the distal section of the guidewire system 100 shown in FIG. 3A, showing multiple pressure sensors 120 and multiple ultrasound sensors 122 disposed on the substrate 124, which is positioned on the wire 102. As shown, the distal-most section of the device can also include a coil 128 and/or atraumatic tip 130. The coil 128 may be a single coil or multiple connected or interwoven coils. Additionally, or alternatively, a polymer material may be positioned on or applied to the distal section of the wire 102. The atraumatic tip 130 forms a sphere or other curved shape to protect against trauma caused by the distal portion of the wire 102. The atraumatic tip 130 may be formed from a polymer adhesive material or solder, for example.

As shown, the wire 102 can include a grind profile such that more distal sections of the wire 102 progress to smaller diameters. For typical guidewire sizes (e.g., 0.014 inches, 0.018 inches, 0.024 inches), the wire 102 may progress to a diameter of about 0.002 inches at the distal end. The distal end of the wire 102 may also be flattened to form a standard "ribbon" shape.

The illustrated embodiment also includes an energy harvester 132. The energy harvester is configured to convert power signals traveling within the wire 102 into regulated DC voltages suitable for the sensors. In at least one embodiment, the power signals traveling through the wire 102 comprise AC power signals that are passed from the power and data coupling device 104 to the wire 102. The energy harvester 132 can also provide other electrical regulation functions such as cutting power to the sensors during a fault or brownout, for example. Additionally, as used herein and unless specified otherwise, the energy harvester 132 is considered a subcomponent of the one or more sensors 121. As such, unless stated otherwise, references to the one or more sensors 121 also refer to the associated circuitry, such as the energy harvester 132.

Additionally, in at least one embodiment, the energy harvester is configured to provide control functions for the one or more sensors 121. For example, a particular signal can be communicated from the power and data coupling device 104 to the energy harvester. The particular signal may comprise a chirp, an impulse function, or some signal at a particular frequency channel. The energy harvester maps the particular signal to a predetermined command and then acts upon that predetermined command. For example, a particular signal may map to a command to cut DC power to one or more rails that are powering one or more sensors. As such, upon receiving the particular signal, the energy harvester stops providing power to the one or more sensors causing the one or more sensors to turn off. Any number of different signals may be mapped to any number of different commands. Additionally, in at least one embodiment, a circuit other than the energy harvester receives, interprets, and/or acts upon the signals.

The length of the wire 102 that includes the substrate 124 (and thus includes sensors) may be about 3 cm to about 30 cm, or more typically about 5 cm to about 15 cm, though these lengths may be varied according to particular application needs. As explained below with respect to the example of FIGS. 4A through 4D, in preferred embodiments the length of the sensor arrangement substantially spans the expected length of lesions/stenoses or other target anatomy. The linear arrangement of pressure sensors 120 can be utilized to provide pressure mapping at targeted anatomy without the need to move the wire 102. Multiple measurements from multiple sensors may be conducted simultaneously and/or continuously. The arrangement of pressure sensors 120 can also be utilized to measure pulse wave velocity (PWV) (e.g., by determining a series of wave peaks and measuring time between peaks) and/or to provide spatial tracking of a pulse waveform.

Methods of Localization Within Target Anatomy

FIGS. 4A through 4D illustrate a sequence showing use of the guidewire system 100 to effectively guide positioning and deployment of a medical device at a targeted anatomical location. In this particular example, the guidewire system 100 is used to properly position a stent 406 at a targeted stenosis 404.

FIG. 4A shows the wire 102 with pressure sensors 120 (other components removed for better visibility) positioned within a vessel 402. The wire 102 is routed through the vessel 402 to a position where the arrangement of pressure sensors 120 span or at least substantially coincide with the stenosis 404. The linear arrangement of the pressure sensors 120 allows the wire 102 to be effectively positioned coincident with the stenosis 404 because the stenosis 404 will cause pressure differences at that portion of the vessel 402, and the user can advance the wire 102 until those pressure differences are read by the sensors 120. For example, where the vessel 402 is a coronary artery, the pressure distal of the stenosis 404 will be somewhat lower than the pressure proximal of the stenosis 404. The wire 102 can be advanced until one or more of the distal-most pressure sensors reach the region of different pressure (e.g., somewhat lower pressure in a coronary vessel stenosis).

The stent 406 is then delivered over the wire 102 toward the stenosis 404. The position of the stent 406 relative to the wire 102 can be determined based on readings from the pressure sensors 120. For example, as the stent 406 is moved distally it will sequentially begin to pass over the pressure sensors 120, causing a change in the pressure reading of the sensors and thereby allowing the user to determine the position of the stent 406 relative to the wire 102.

FIG. 4B shows the stent 406 positioned farther within the vessel 402 to its target location. The delivery catheter 408 is also shown. For stent delivery applications such as shown here, the delivery catheter 408 may be a balloon catheter, or the stent 406 may be a self-expanding stent. Other stent types and stent delivery means as known in the art may be utilized. Proper positioning of the stent 406 is possible because the position of the wire 102 relative to the stenosis 404 is known based upon readings received from the pressure sensors 120. Additionally, determining where the stent 406 is positioned relative to the wire 102 thus allows determination of the position of the stent 406 relative to the stenosis 404.

Once the stent 406 is determined to be in the proper position relative to the target stenosis 404, the stent 406 may be deployed as shown in FIG. 4C. After deployment, the wire 102 may remain in place for a time during post-stent assessment. The wire 102 may then be retracted from the vessel 402, leaving the stent 406 in place as shown in FIG. 4D.

Due to the sensors positioned along the length of the wire 102, the guidewire system 100 can therefore provide a localized reference frame (i.e., a reference frame within the localized anatomy of the target) for guiding positioning of a medical device. This is beneficial because the target anatomy is not always static. In vasculature applications, for example, heartbeats cause the vessel to constantly move. The localized reference frame defined by the distal section of the guidewire system 100 moves substantially with the target anatomy in which it is placed, removing many positioning complications and thereby improving the ability to position stents and/or other medical devices.

This localized reference frame is also relatively stable because the wire 102 does not need to be moved to make sequential measurements. Additionally, the sensors 120 are able to continuously and simultaneously provide sensor data signals during the placement of the stent, or other medical device. This allows a medical practitioner to guide the stent, or other medical device, in real time to the desired position within the body. That is, the linear arrangement of the sensors 120 allows multiple measurements without the need to "pull back" the wire 102 to make measurements in other positions. Moreover, as described above, the system may be configured to provide multiple measurements from multiple sensors simultaneously, eliminating the need to even do a "virtual pull back" of sequential measurements along the length of sensors.

The procedure illustrated in FIGS. 4A through 4D is one example of using the guidewire system 100 for localization within target anatomy. The guidewire system 100 and/or catheter system 200 may be utilized in other applications where the localization features of the system would be beneficial. For example, localization features described herein may be utilized to aid in proper placement of a PICC catheter or central venous catheter at a targeted site such as the cavoatrial junction.

The Elongated Conductive Member as a Power and Data Conductive Path

Figure 5:
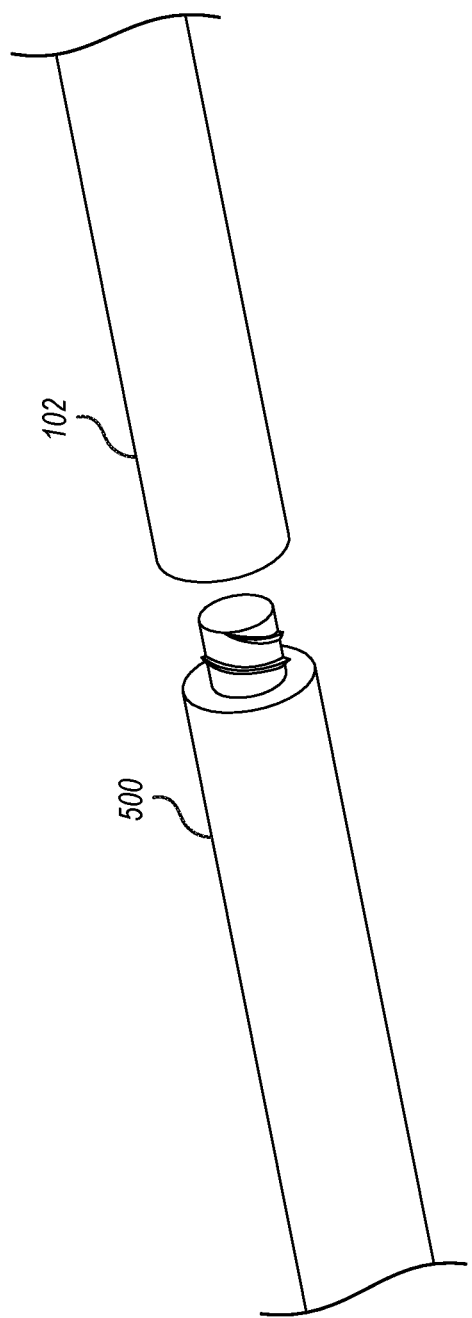
FIG. 5 illustrates an extension wire being added to the wire.

FIG. 5 illustrates an extension wire 500 being added to the wire 102. In various use cases, it may be necessary to extend the wire 102 in order to better position and/or manipulate the wire 102 within a patient's body. The depicted extension wire 500 may be coupled to the wire 102 through any number of different physical couplings, including, but not limited to, a threaded connection, a magnetic connection, a press-fit connection, a snap connection, or an adhesive connection.

In at least one embodiment, the resulting physical coupling results in a continuous conductive pathway from the extension wire 500 to the wire 102. As such, due to at least the physical coupling and the electrical coupling, both the extension wire 500 and the wire 102 may be jointly considered and referred to as the "wire 102." More specifically, electrical signals applied to the extension wire 500 will propagate from the extension wire 500 to the wire 102. Accordingly, unless stated otherwise, all descriptions of the wire 102 provided herein also apply when an extension wire 500 is attached to the wire 102. Additionally, it will be appreciated that any elongated conductive member disclosed herein may comprises multiple extensions that are removably attached to each other.

In at least one embodiment, the guidewire system 100 comprises a medical device system for concurrent power and data transfer. In particular, the guidewire system 100 may comprise a type of elongated conductive member. As used herein, the elongated conductive member comprises a proximal portion and a distal portion. At least a portion of the elongated conductive member is configured for insertion within an intraluminal space. Additionally, both the proximal portion and the distal portion of elongated conductive member may be electrically conductive.

In at least one embodiment, the elongated conductive member comprises a single conductive pathway extending from the proximal portion to the distal portion. For instance, the single conductive pathway may comprise a stainless-steel wire 102 within the guidewire system 100. Additionally or alternatively, the elongated conductive member comprises multiple conductive pathways extending from the proximal portion to the distal portion. For instance, the catheter system 200 may comprise multiple wires integrated within the structure of the catheter 202. Additionally, in at least one embodiment, the elongated conductive member comprises a first conductive pathway for use as a power channel and a second conductive pathway for user as a signal channel, both the first conductive pathway and the second conductive pathway extending from the proximal portion to the distal portion.

As used herein, the elongated conductive member comprises any conductive component that is longer than it is wide. For example, the elongated conductive member includes the wire 102. For the sake of example and explanation, the elongated conductive member may also be referred to as the wire 102; however, one will appreciate the wire 102 is a subset of possible elongated conductive members. For example, the elongated conductive member may also comprise catheter 202.

As described above, one or more sensors 121 may be in electrical connection with the elongated conductive member. Additionally, the medical device, which includes the elongated conductive member, may also comprise one or more electrical components that are physically configured such that when activated, the one or more electrical components cause the medical device system to perform various actions. As used herein, the one or more electrical components may comprise discrete circuit components, digital circuit components, analog circuit components, processor(s), or any combination thereof. The one or more electrical components may be integrated within control unit 112 or 212, within the external device 110, and/or on the elongated conductive member. Activating the one or more electrical components may comprise providing power to the one or more electrical components.

In at least one embodiment, the one or more electrical components cause the medical device system to allocate a signal space into a plurality of unique contiguous segments. Each segment within the signal space comprises a portion of the signal space that may be used for the purposes of communicating data, power, or other information. The signal space may comprise a frequency-domain space, a time-domain space, or any other space capable of carrying a signal. Additionally, allocating the signal space may comprise dynamically identifying signal channels of interest. Alternatively, allocating the signal space may comprise providing electrical components that are configured to statically define the signal space.

Figure 6A:
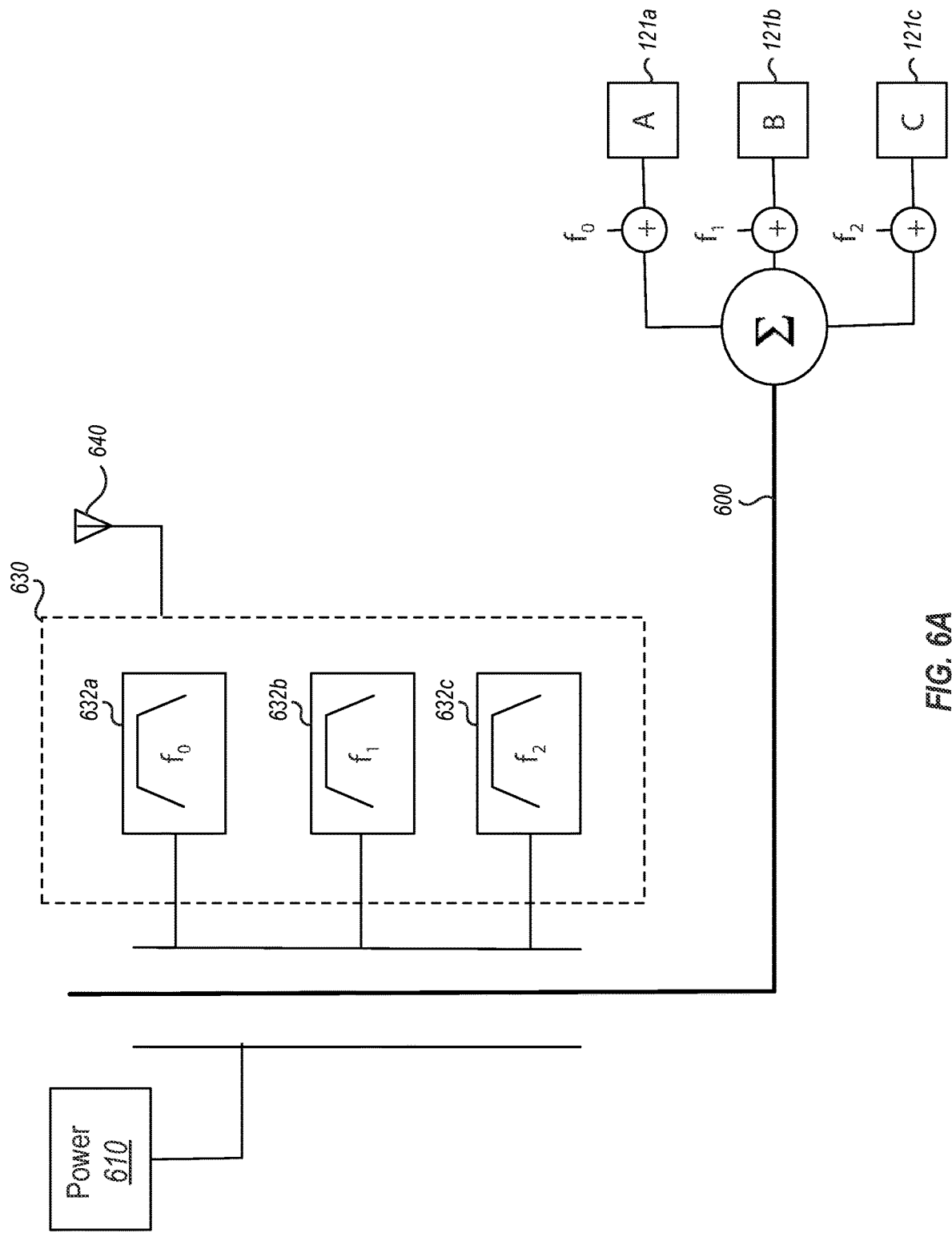
FIG. 6A illustrates an electrical schematic diagram of a medical device.
Figure 6B:
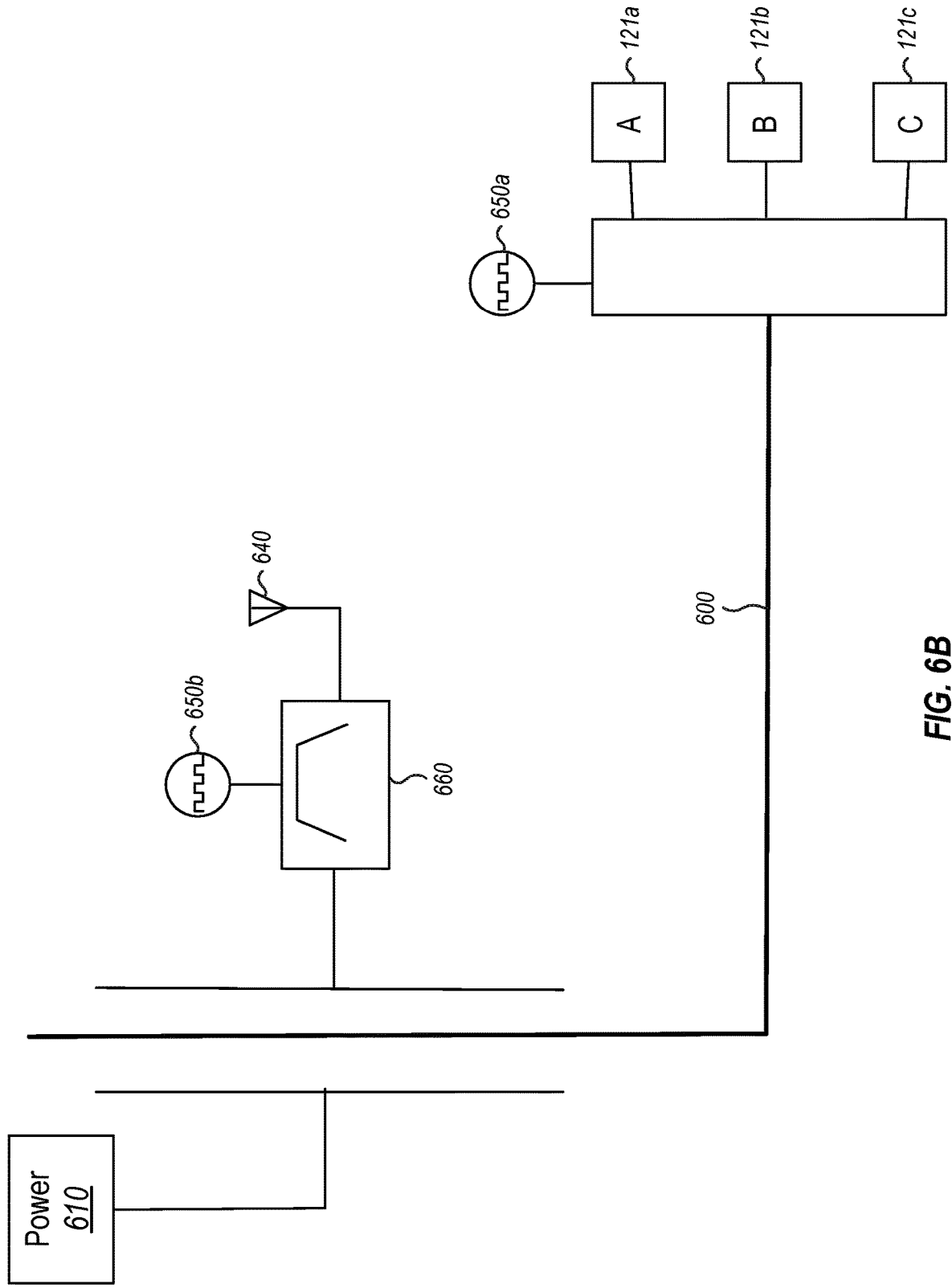
FIG. 6B illustrates another electrical schematic diagram of the medical device.
Figure 7:
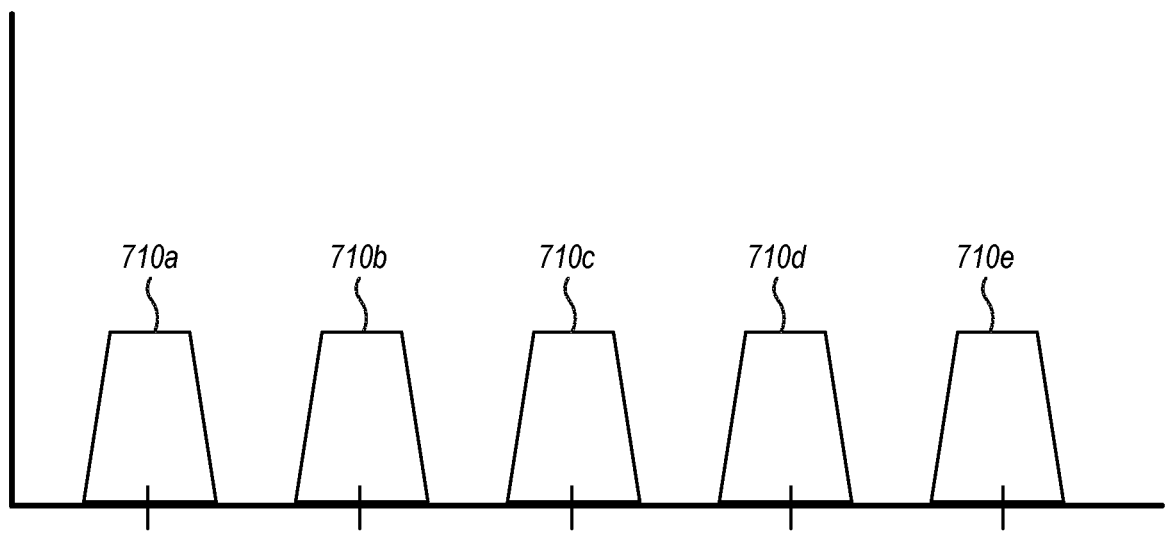
FIG. 7 illustrates channels configured for utilization by the medical device.

For example, FIGS. 6A and 6B illustrate different embodiments of an electrical schematic diagram of the medical device. FIG. 7 illustrates channels configured for utilization by the medical device. In at least one embodiment, the one or more electrical components uniquely allocate each of the plurality of unique contiguous segments to one of (i) one or more power channels or (ii) one or more signal channels. In at least one embodiment, uniquely allocating refers to each contiguous segment being allocated as either a power channel or a signal channel. In some embodiments, there may be multiple power channels and multiple signal channels.

FIG. 6A depicts a schematic of a frequency-based medical device system. In particular, the one or more electrical components cause the medical device system to allocate a signal space into the plurality of unique contiguous segments by designating a plurality of unique contiguous regions of frequency (e.g., 710(*a-e*)). The one or more electrical components further cause the medical device system to uniquely allocate each of the plurality of unique contiguous regions of frequency to one of (i) the one or more power channels or (ii) the one or more signal channels.

FIG. 6B depicts a schematic of a time-based medical device system. In particular, the one or more electrical components cause the medical device system to allocate a signal space into the plurality of unique contiguous segments by designating a plurality of unique contiguous time slots (e.g., 710(*a-e*)). The one or more electrical components further cause the medical device system to uniquely allocate each of the plurality of unique contiguous time slots to one of (i) the one or more power channels or (ii) the one or more signal channels.

FIG. 7 illustrates that the signal space 700 may comprise multiple unique contiguous segments in the form of multiple frequency channels 710(*a-e*). Each frequency channel may be allocated as a power channel for providing power to the electronic devices located on the elongated conductive member or may be allocated as a signal channel for receiving data from the electronic devices on the elongated conductive member. In at least one embodiment, the electronic devices comprise sensors 121.

Additionally or alternatively, the signal space 700 may comprise multiple unique contiguous segments in the form of time slots 710(*a-e*). Each time slot may be defined based on a clock. Additionally, each time slot may be allocated as a power channel for providing power to electronic devices located on the elongated conductive member or may be allocated as a signal channel for receiving data from the electronic devices on the elongated conductive member.

For example, FIGS. 6A and 6B depict an elongated conductive member 600 that is coupled to a power source 610. The power source 610 may be configured to send electrical signals, via the elongated conductive member 600, to one or more sensors 121(*a-c*) that are in electrical connection with the elongated conductive member 600. In particular, the power source 610 may send AC electrical signals within a particular unique contiguous segment, such as frequency channel 710*a*. In at least one embodiment, the elongated conductive member 600 is capacitively coupled to the power source 610 such that no direct physical contact is present between the elongated conductive member 600 and the power source 610. Alternatively, in at least one embodiment, a direct physical contact may be present between the elongated conductive member 600 and the power source 610.

Returning now to FIG. 3C, an elongated conductive member, in the form of the wire 102, is shown to include an energy harvester 132. As used herein, an energy harvester 132 refers to an electronic circuit that is configured to harvest energy from an allocated power channel. In particular, an energy harvester 132 may comprise an electronic circuit to harvest energy from the electrical signals within at least one of the one or more power channels—in this example, frequency channel 710*a*. The harvested energy is then provided to the at least one of the one or more sensors 121.

In at least one embodiment, the power source 610 transmits energy within the at least one of the one or more power channels and provides power to all of the one or more sensors 121 through the at least one of the one or more power channels. As such, each sensor of the one or more sensors harvests energy from the particular unique contiguous segment of the signal space that is represented by the at least one of the one or more power channels.

Additionally or alternatively, in at least one embodiment, the power source 610 transmits energy within a first power channel of the one or more power channels (e.g., 710*a*), wherein the first power channel of the one or more power channels comprises a first unique contiguous segment of the signal space. Additionally, the power source 610 transmits energy within a second power channel of the one or more power channels (e.g., 710*b*), wherein the second power channel of the one or more power channels comprises a second unique contiguous segment of the signal space. The elongated conductive member 600 then provides energy to a first subset of the one or more sensors through the first power channel of the one or more power channel. Each sensor of the first subset of the one or more sensors is configured to harvest energy from the first unique contiguous segment of the signal space. Similarly, the elongated conductive member 600 provides energy to a second subset of the one or more sensors through the second power channel of the one or more power channels. Each sensor of second subset of the one or more sensors is configured to harvest energy from the second unique contiguous segment of the signal space.

Accordingly, in at least one embodiment, the elongated conductive member 600 provides different sets of sensors power through independent power channels. This provides a user with the ability to selectively activate all of the sensors simultaneously or to only activate subsets of the sensors at different times. Additionally, the one or more sensors may comprise at least a first sensor of a first type and a second sensor of a second, different type. Accordingly, in at least one embodiment, a user can activate sensors based upon sensor type. As disclosed herein, this selective control of the sensors and communication with the sensors may be performed over a single conductive path, such as wire 102.

Once at least one sensor from the one or more sensors 121 begins to receive the harvested energy, the at least one sensor will begin to generate data signals based upon readings received by the at least one sensor. FIG. 6A depicts a set of sensors 121(*a-c*) that each transmit along the elongated conductive member 600 at a particular frequency. For example, sensor 121*a* is added to frequency $f_0$ and then summed with any other data signals that are each in their own frequency. One will appreciate that his system allows multiple data signals to be communicated simultaneously in parallel via the elongated conductive member 600.

Additionally, FIG. 6A shows that the one or more electrical components cause the medical device system to isolate transmitted data signals from at least one of the one or more signal channels. As stated above, the data signals are transmitted via the elongated conductive member 600 and generated by the one or more sensors 121(*a-c*). The elongated conductive member 600 is also coupled with a power and data coupling device 630 (also referred to as a proximal device 204 in FIG. 2). In at least one embodiment, the elongated conductive member 600 is capacitively coupled to the power and data coupling device 630 such that no physical connection is present between the elongated conductive member 600 and the power and data coupling device 630. Alternatively, in at least one embodiment, a physical connection may be present between the elongated conductive member 600 and the power and data coupling device 630.

The power and data coupling device 630 comprises multiple frequency filters 632(*a-c*) that allow it to isolate the respective data signals that are communicated along the elongated conductive member 600. Each of the multiple frequency filters 632(*a-c*) may also function as an amplifier that is configured to amplify the data signals. Additionally or alternatively, in at least one embodiment, the power and data coupling device 630 isolates multiple transmitted data signals in parallel. Each data signal from the multiple data signals is associated with a different unique contiguous region of frequency selected from the plurality of unique contiguous regions of frequency. The power and data coupling device 630 further comprises a transmitter 640 that is configured to communicate the isolated data signals to the external device 110 for display and/or processing.

FIG. 6B depicts a set of sensors 121(*a-c*) that each transmit along the elongated conductive member 600 within a time slot. For example, each sensor 121(*a-c*) communicates data signals via the elongated conductive member 600 at a particular time slot that is determined by a clock signal 650*a*. Additionally, FIG. 6B shows that the elongated conductive member 600 is also coupled with a power and data coupling device 630. The power and data coupling device 630 comprises a filter 660 that is in communication with a clock 650*b*, which clock is synchronized with clock 650*a*. The combination of the synchronized clocks 650*a*, 650*b* and the filter 660 allow the power and data coupling device 630 to isolate the data signals within each respective time slot. The power and data coupling device 630 further comprises a transmitter 640 that is configured to communicate the isolated data signals to the external device 110 for display and/or processing.

The Power and Data Coupling Device

FIGS. 8A-8D depict various embodiments of a power and data coupling device 104. In these particular depicted embodiments, the power and data coupling device comprises a hemostatic valve. However, in view of the disclosure provided herein, one will appreciate that a standard valve, or other in-line component (that doesn't necessarily include a valve), can provide similar functionality and structure. As used herein, the power and data coupling device comprises a device that transmits power and data from a first conductive surface to a second conductive surface through electric fields. Additionally, the power and data coupling device 104 may provide power and receive data signals from sensors disposed on a medical device.

For example, the power and data coupling device may be capacitively coupled with a medical device, such as wire 102. The capacitive coupling allows the power and data coupling device to provide power to the medical device and to receive and/or transmit data signals to the medical device. In particular, in at least one embodiment, the first conductive surface is not in physical contact with the second conductive surface. Though, one will appreciate, in at least one embodiment the first conductive surface may be in physical contact with the second conductive surface.

As described above, the lack of direct physical contact between the first conductive surface and the second conductive surface allows medical practitioner to translate a second elongated conductive member, such as stent, over or adjacent to a second conductive surface, such as a wire 102 in a guidewire system 100. Additionally, the capacitive coupling between the first conductive surface and the second conductive surface allows an external device 110 to continue receiving the signals while the second elongated conductive member (e.g., the stent) is positioned between the first conductive surface and the second conductive surface (e.g., the wire 102).

Figure 8A:
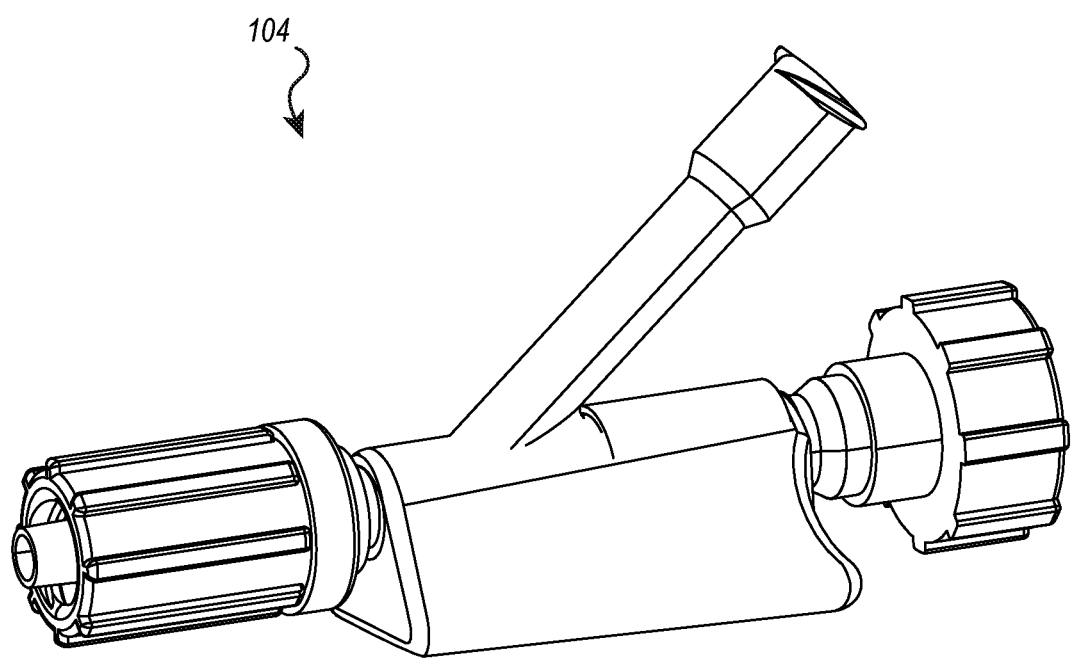
FIGS. 8A-8E depict various embodiments of a power and data coupling device.
Figure 8B:
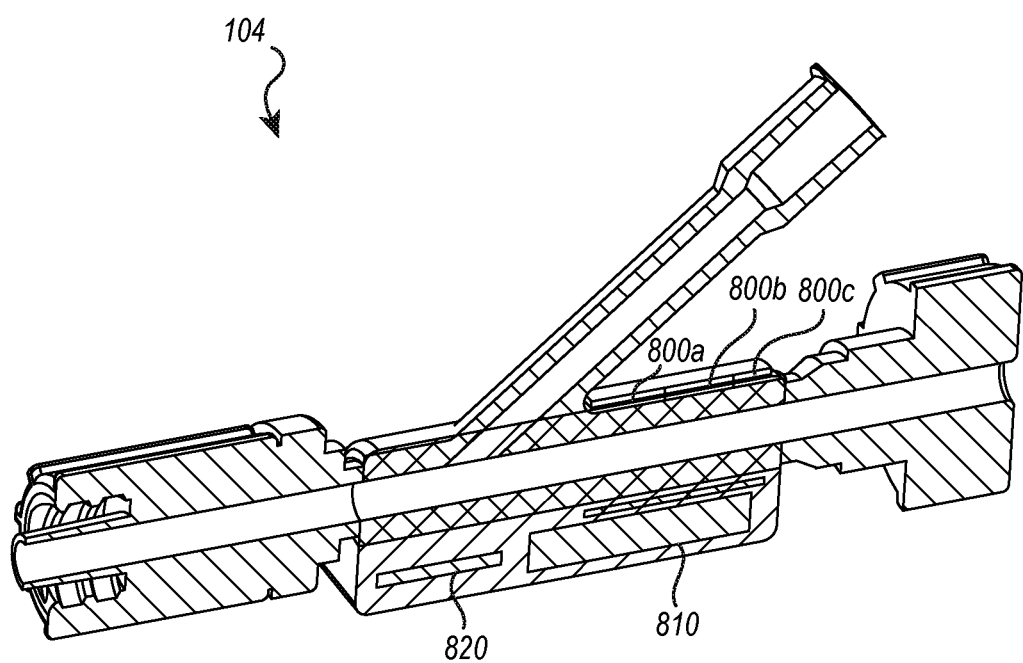

For example, FIG. 8B depicts a cross-sectional view of a power and data coupling device 104. The depicted power and data coupling device 104 may comprise a first conductive surface 800*a* integrated into the power and data coupling device 104 and configured to couple via an electric field with a second conductive surface. The coupling via the electric field may comprise a capacitive coupling.

Figure 8C:
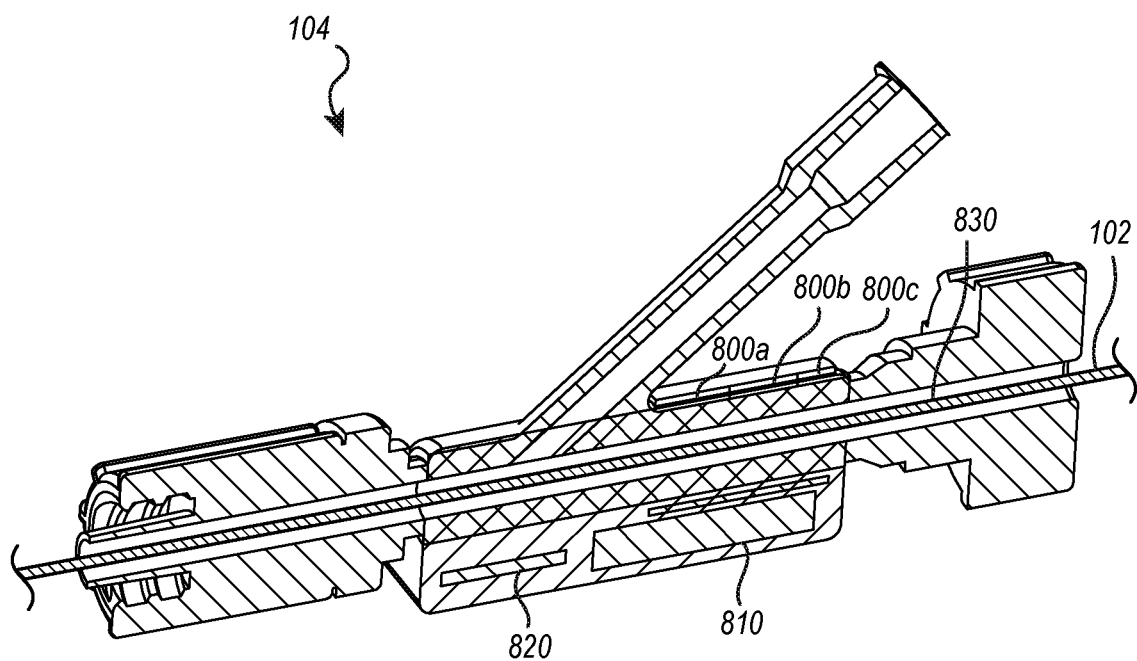
Figure 8D:
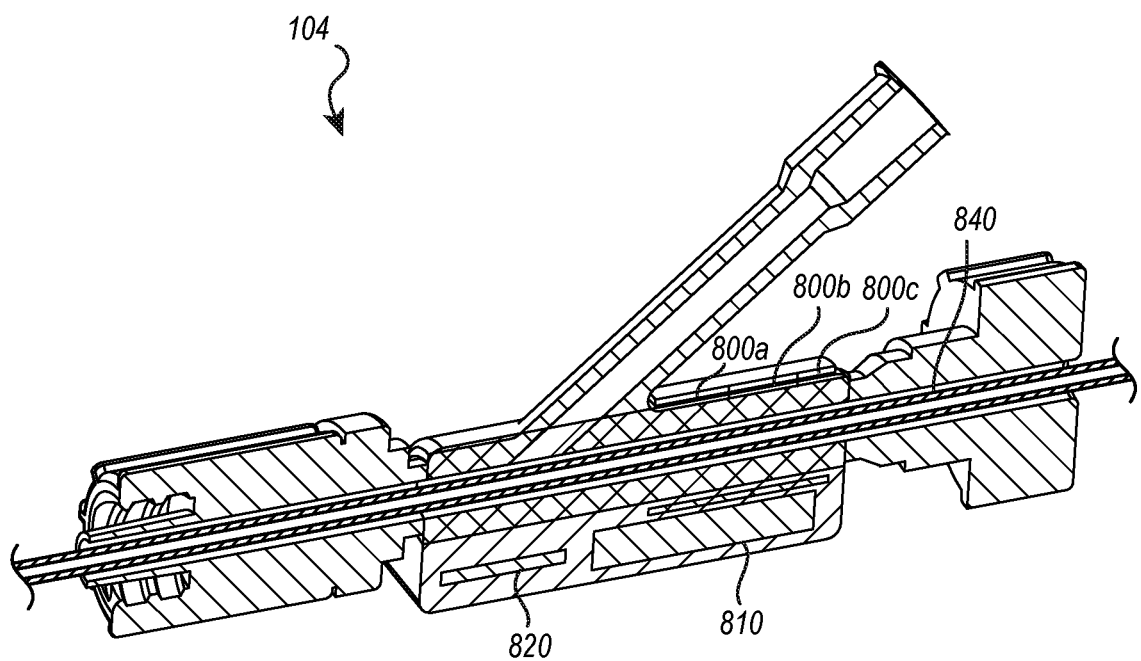

For example, FIG. 8C depicts a second conductive surface 830 in the form of a wire 102. As described above, a guidewire system 100 may comprise a conductive wire 102. Similarly, FIG. 8D depicts a second conductive surface 840 in the form of a catheter 202. As described above, a catheter system 200 may comprise a catheter 202 with conductive components, such as wire embedded within the catheter itself allowing the first conductive surface 800a to capacitively couple with the catheter 202. In the depicted example, at least a portion of the second conductive surface 834, 840 is encompassed by the first conductive surface 800a, but one will appreciate that such a configuration is not required for operation of the medical device as disclosed herein. For example, the first conductive surface 800 may enclose a portion of the second conductive surface 830, 840, may be adjacent to the second conductive surface 830, 840, may be enclosed by the second conductive surface 830, 840, or may otherwise be positioned with respect to the second conductive surface 830, 840 such that a capacitive coupling occurs between the first conductive surface 800 and the second conductive surface 830, 840. Additionally, one will appreciate that the wire 102 and the catheter 202 are only provided as examples of second conductive surfaces, and that other medical devices may also be utilized as second conductive surfaces.

In at least one embodiment, the second conductive surface 830, 840 may be translatable with respect to the first conductive surface 800a. For example, the wire 102 may be translatable with respect to both the first conductive surface 800a and the entire power and data coupling device 104 such that the power and data coupling device 104 is able to provide power and data coupling the wire 102 while the wire 102 is being translated. One will appreciate that such a feature allows the wire 102 to be positioned and moved within a human body while the power and data coupling device continues to provide power to and receive data signals from the one or more sensors 121 on the wire 102.

As described above, the first conductive surface 800a may be connected to a power source for providing power, through the electric field, to the second conductive surface. For example, FIG. 8B depicts a battery 810 integrated within the power and data coupling device 104. In additional or alternative embodiments, the power and data coupling device 104 may be physically connected to a wired power source, such as an outlet. One will appreciate, though, that integrating a battery 810 within the power and data coupling device 104 provide significantly better mobility and ease of use when using the power and data coupling device 104 during a medical procedure.

The first conductive surface 800a may be configured to radiate a time-varying electric field that is configured to convey power to the second conductive surface 830, 840. For example, the first conductive surface 800a may capacitively couple with the second conductive surface 830, 840 such that the first conductive surface 800a induces a charge on the second conductive surface 830, 840. The resulting capacitive coupling can convey power, or energy, to the one or more sensors 121 disposed on the wire 102.

Additionally, the first conductive surface 800a may be connected to a pick-up that is configured to receive signals from the second conductive surface 830, 840. For example, FIG. 8B depicts a transmitter 820 that is in communication with the first conductive surface 800a through a pick-up. The transmitter 820 is able to receive data signals, through the pick-up, from the first conductive surface and transmit those data signals to an external device 110. In at least one embodiment, the transmitter 820 also comprises a signal collector that is configured to isolate the signals (also referred to as data signals) using the methods described above. Additionally or alternatively, the signal collector may be located, at least in part, at the external device 110. Similarly, in at least one embodiment, the transmitter 820 also comprises one or more processors configured to process the signals. Such processing may comprise various signal processing and analysis of the signals. Additionally or alternatively, the one or more processors may be located, at least in part, within the external device 110.

Disclosed embodiments provide for a highly versatile and innovative solution for providing power to and receiving data signals from a medical device. For example, the first conductive surface 800a may be configured to simultaneously (i) provide a power signal to the second conductive surface 830, 840 and (ii) receive a data signal from the second conductive surface 830, 840. Further, the first conductive surface 800a may be configured to simultaneously (i) provide multiple, different power signals to the second conductive surface and (ii) receive multiple, different data signals from the second conductive surface. Each power signal in the multiple, different power signals may be configured to provide power to a different set of medical sensors, and each data signal in the multiple, different data signals may provide data from a different group of medical sensors.

As explained above with respect to FIGS. 6A and 6B, multiple different segments within the signal space may be allocated as power channels or signal channels. The power and data coupling device 104 is able to selectively provide power to a particular power channel in order to power a particular set of sensors. Similarly, the power and data coupling device 104 is able to receive, in parallel, real-time data signals from the one or more sensors 121 that are being powered through the power channels.

FIGS. 8B-8D also show that first conductive surface may comprises a plurality of physically separate conductive surfaces 800a, 800b, 800c. One will appreciate that any of the physically separate conductive surfaces 800a, 800b, 800c may comprise a conductive surface in a capacitor and as such may be referred to as "the first conductive surface." In at least one embodiment, each conductive surface 800a, 800b, 800c selected from the plurality of physically separate conductive surfaces may be configured to receive a data signal from a particular, different set of medical sensors 121. For example, in some circumstance utilizing specific conductive surface 800a, 800b, 800c for specific data signals may allow for a lower signal-to-noise ratio.

Further, individual conductive surface 800a, 800b, 800c may be specifically designed for particular functions. For example, a first conductive surface 800a selected from the plurality of physically separate conductive surfaces may be configured to provide power to at least one medical sensor and a second conductive surface 800b selected from the plurality of physically separate conductive surfaces may be configured to receive a data signal from the at least one medical sensor. Accordingly, the first conductive surface 800a may be specifically designed to provide power, while the second conductive surface 800b may be designed to receive data signals. Such design specification may relate to the size of the individual surface, the material construction of the individual surface, and/or the shape of the individual surface.

Figure 8E:
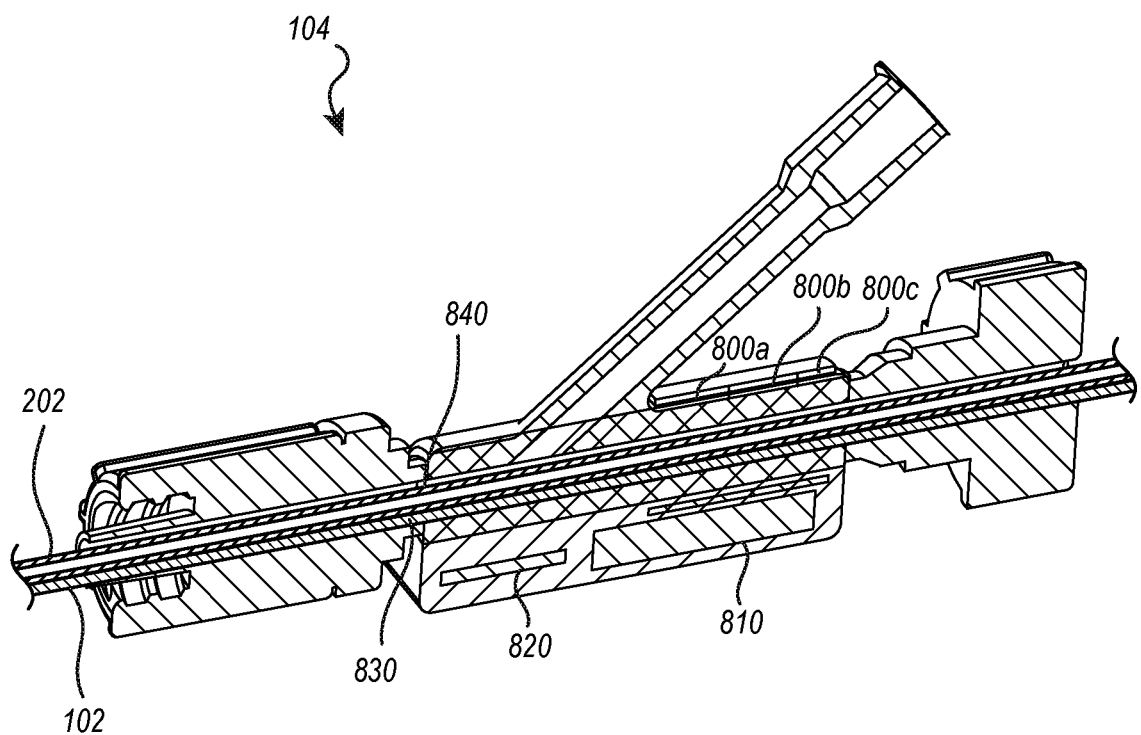

FIG. 8E depicts an embodiment of the power and data coupling device 104 that encloses one or more elongated conductive members. In particular, the depicted embodiment shows a wire 102 and a catheter 202 enclosed within the power and data coupling device 104. In the depicted embodiment, the wire 102 may be coupled through a "rapid exchange" coupling with a catheter 202. The rapid exchange coupling comprises a distal portion of the catheter 202 enclosing the wire 102 and a proximal portion of the wire 102 running adjacent to a proximal portion of the catheter 202. In an alternative embodiment, the wire 102 may be coupled through an over-the-wire (OTW) coupling with a catheter 202, such the catheter 202 encloses the wire 102 at least from the power and data coupling device 104 to the distal portion of the catheter 202. In either case, the power and data coupling device 104 is configured to couple to one or more of a conductive surface 830 in the wire 102 and/or a conductive surface 840 in the catheter 202.

In at least one embodiment, the catheter 202 may not comprise a conductive surface 840, while the wire 102 does comprise a conductive surface. In such a case, the wire 102 may be configured to provide energy to sensors that are disposed on the distal portion of the catheter 202. Further, in at least one embodiment, multiple power and data coupling devices 104 may be used during a single procedure such that a given elongated conductive member travels through multiple power and data coupling devices 104 and/or multiple elongated conductive members travel through different power and data coupling devices 104.

Figure 9:
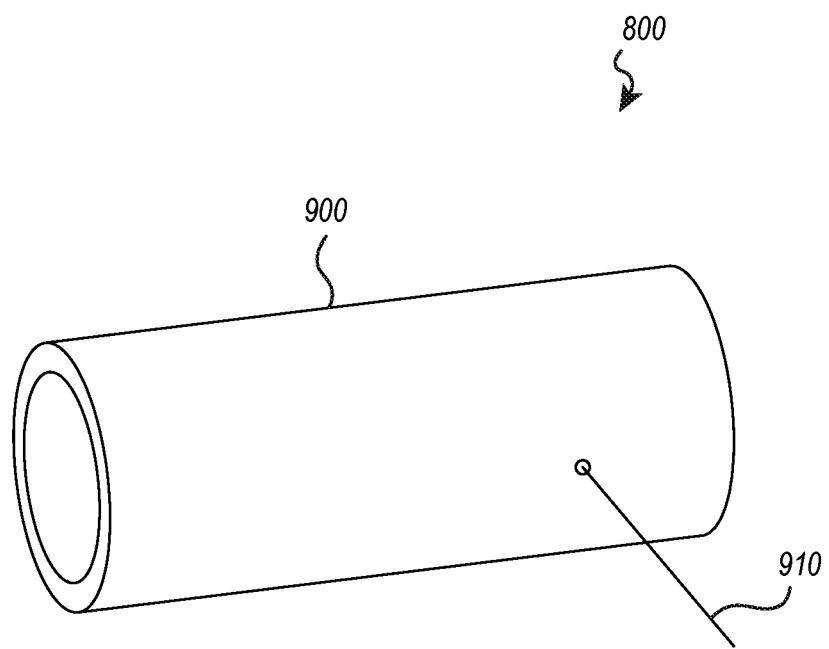
FIG. 9 depicts another embodiment of a power and data coupling device.

FIG. 9 depicts another embodiment of a power and data coupling device 104 in the form of a tube 900. In particular, FIG. 9 depicts a conductive tube 900 being used as the first conductive surface 800. A signal input line 910 is connecting to the conductive tube 900 and can provide power to the tube 900 and receive signals from the tube 900. One of skill in the art will appreciate that the conductive tube is provided only as an example of a power and data coupling device 104. In various additional or alternative embodiments, the power and data coupling device 104 may comprise any device with a first conductive surface that is configured to couple to a second conductive surface of a medical device for the sake of providing power to the medical device and/or receiving data signals from the medical device.

Figure 10A:
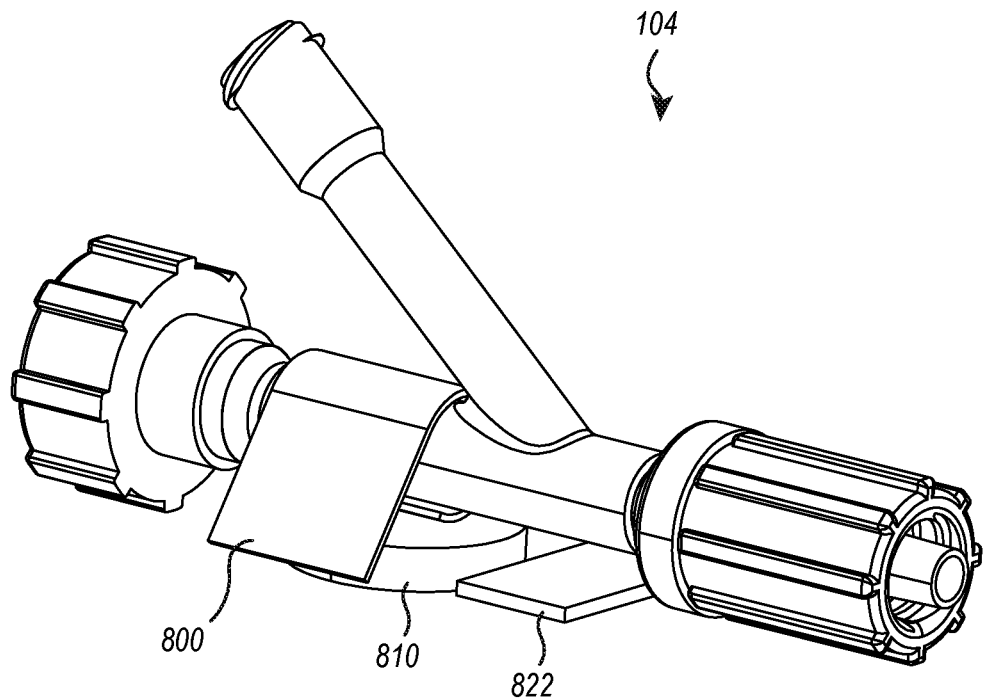
FIGS. 10A-10C depict embodiment of conductive surfaces within a power and data coupling device.
Figure 10B:
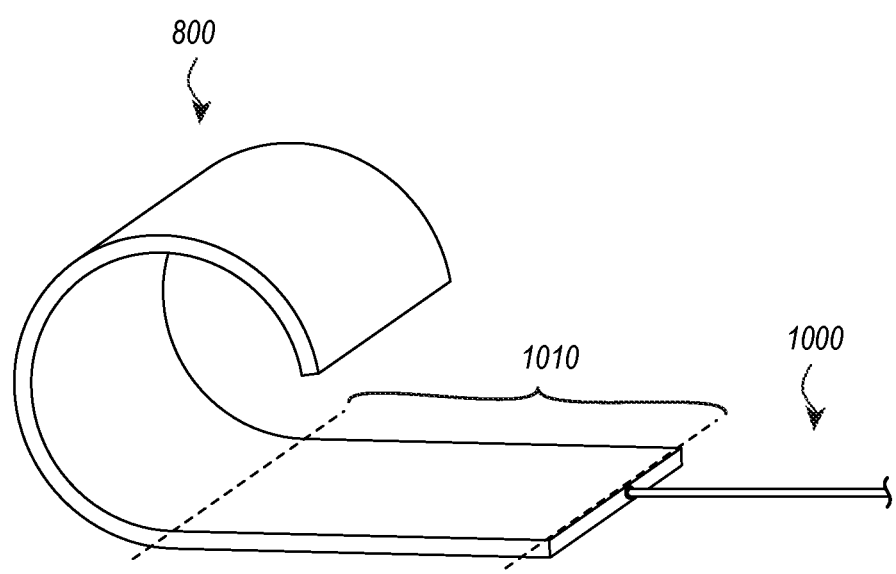
Figure 10C:
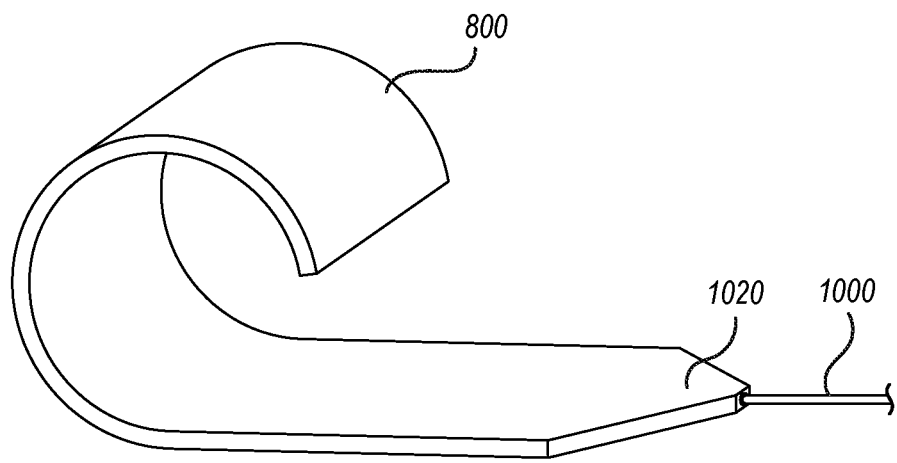

FIGS. 10A-10C depict embodiments of conductive surfaces 800 within a power and data coupling device 104. Similar to FIGS. 8A-8D, the power and data coupling device 104 comprises a battery 810 and a transmitter 820. However, in FIG. 10A, the outer shell has been removed from the power and data coupling device 104. One will appreciate that the depicted battery 810 and transmitter 820 are shown in a simplified form for the sake of example.

As depicted in FIG. 10B, in at least one embodiment, the first conductive surface 800 comprises a curl-shape. A power input line 1000 is physically connected to a feed 1010 on the first conductive surface 800. The power input line 1000 may both provide energy to the conductive surface 800 and receives data signals from the first conductive surface 800.

In at least one embodiment, the feed 1010 is sized such that it substantially matches an impedance of a coupling between the first conductive surface 800 and a second conductive surface 830, 840. One will appreciate that the coupling between the first conductive surface 800 and a second conductive surface 830, 840 may be defined, at least in part, by the frequency of the signal applied by the power input line. For example, the power input line 1000 may provide a power signal to the feed 1010 at a frequency of 40 MHz to 80 Mhz. It has been observed that such a frequency range provides technical benefits relating to the efficiency with which power is provided to sensors attached to an elongated conductive member, such as a wire 102 or catheter 202. In at least one embodiment, properly sizing the feed also provides significant benefits in the efficiency with which energy can be provided by the power input line 1000 to sensors attached to an elongated conductive member.

In additional or alternative embodiments, the first conductive surface 800 comprises any number of different shapes, including a ring with a feed 1010 extending from an outer surface of the ring. Additionally, in at least one embodiment, the feed 1010 may comprise non-planar surface, for example, ripples, in order to provide a greater surface area to the feed 1010 while maintaining or decreasing the total distance that the feed 1010 extends away from the first conductive surface 800.

FIG. 10C depicts an embodiment of a first conductive surface 800 that comprises a triangular shaped feed 1020 that is connected to the power input line 1000. In at least one embodiment, the triangular shaped feed 1020 may increase the efficiency of the distribution of the energy from the power input line 1000 to the first conductive surface 800.

In at least one embodiment, the power and data coupling device 104 comprises an indicator for indicating information relating to the operation of the power and data coupling device 104 or the elongated conductive member. The indicator may comprise a sound alert, a visual alert (e.g., a light), a communication to an external device that performs an alert function and/or any other type of alert. For example, the transmitter 820 may comprise some processing capability that can detect an interruption in power traveling through the power and data coupling device 104 and/or a poor quality of data signals being received by the power and data coupling device 104. In such cases, the power and data coupling device 104 may cause an indication of an alert to be issued in order to notify a user of the issue.

Figure 11A:
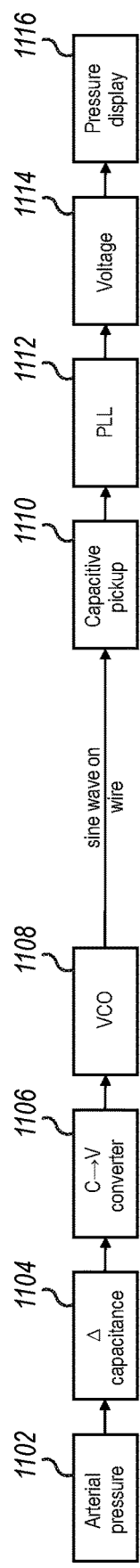
FIGS. 11A-11C depicts various electrical schematic diagrams of the medical device.
Figure 11B:
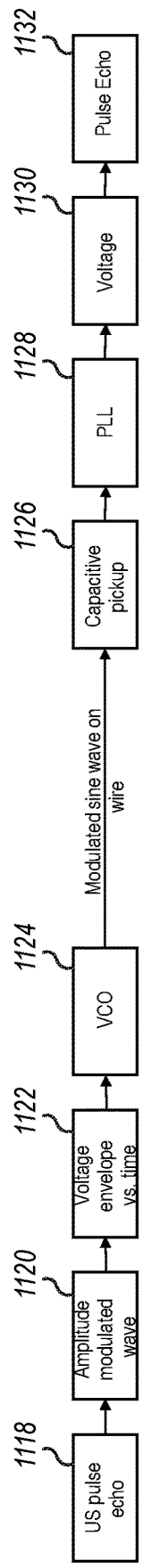
Figure 11C:

FIGS. 11A-11C depicts various signal schematic diagrams of the guidewire system 100. One will appreciate, however, that similar electrical circuits could also be integrated into any elongated conductive member 600, including a catheter 202. The schematic of FIG. 11A depicts a circuit for gathering and displaying arterial pressure. In particular, the arterial pressure 1102 is gathered by a capacitive pressure sensor 1104, one will appreciate that any number of different pressure sensors types may alternatively be used. The capacitive pressure sensor 1104 utilizes a capacitance-to-voltage converter 1106 to generate a particular voltage based upon the particular capacitance that is measured by the capacitive pressure sensor 1104.

The particular voltage is processed through a voltage-controlled oscillator ("VCO") 1108 to generate a particular waveform. The particular waveform is then transmitted via the elongated conductive member 600 from the distal portion of the elongated conductive member 600 to the proximal portion of the elongated conductive member 600. In this example, the elongated conductive member 600 comprises the wire 102 within the guidewire system 100. In at least one embodiment, the particular waveform is transmitted within a particular unique contiguous segment of a signal space, such as a signal channel as defined by a particular frequency channel.

Once the particular waveform reaches the proximal portion of the elongated conductive member 600, a capacitive pickup 1110 detects the particular waveform within the particular unique contiguous segment of a signal space. In at least one embodiment, the capacitive pickup 1110 is integrated within the power and data coupling device 630. In at least one embodiment, the power and data coupling device 630 may be in capacitive communication with the elongated conductive member 600 through changing electric fields. The capacitive pickup 1110 communicates the detected waveform to a phase-lock loop (PLL) 1112 which is then turned into a voltage 1114. The resulting voltage 1114 can then be processed and displayed 1116 as a pressure reading to an end-user.

FIG. 11B depicts a circuit for gathering and displaying a pulse echo. In particular, the pulse echo is gathered by an ultrasound pulse echo sensor 1118. The ultrasound pulse echo sensor 1118 generates an amplitude modulated wave 1120. A voltage envelope versus time 1122 is then created. In at least one embodiment, the voltage envelope versus time is created using a Hilbert transform circuit. The resulting signal is processed through a voltage-controlled oscillator ("VCO") 1124 to generate a representative signal. The representative signal is then transmitted via the elongated conductive member 600 from the distal portion of the elongated conductive member 600 to the proximal portion of the elongated conductive member 600. Similar to the above example, in this example, the elongated conductive member 600 comprises the wire 102 within the guidewire system 100. In at least one embodiment, the representative signal is transmitted within a particular unique contiguous segment of a signal space, such as a signal channel as defined by a particular frequency channel.

Once the particular waveform reaches the proximal portion of the elongated conductive member 600, a capacitive pickup 1126 detects the representative signal within the particular unique contiguous segment of a signal space. In at least one embodiment, the capacitive pickup 1126 is integrated within the power and data coupling device 630. Additionally, the power and data coupling device 630 may be in capacitive communication with the elongated conductive member 600 through changing electric fields. The capacitive pickup 1126 communicates the detected signal to a phase-lock loop (PLL) 1128 which is then turned into a voltage 1130. The resulting voltage 1130 can then be processed and displayed 1132 as a pulse echo reading to an end-user.

FIG. 11C depicts a circuit for providing power to the one or more sensors 121. As such, in contrast to FIGS. 11A and 11B, FIG. 11C starts from the proximal portion of the elongated conductive member 600 and transmits towards the distal portion of the elongated conductive member 600. In particular, a frequency generation circuit 1134 creates a power signal within a particular unique contiguous segment of a signal space, the particular unique contiguous segment comprising a particular power channel. The generated AC signal is communicated to a power amplifier 1136 to generate a particular AC power signal within the particular power channel. The AC power signal is capacitively coupled 1138 to the elongated conductive member 600 and then transmitted, via the elongated conductive member 600, to the one or more sensors 121 at the distal portion of the elongated conductive member 600.

Once the AC power signal reaches the distal portion of the elongated conductive member 600, the AC power signal is rectified 1140 and processed through a qualification/smoothing circuit 1142. The resulting DC power signal 1144 is then provided to the one or more sensors 1146, 121, 220.

One will appreciate that each of the above-described circuits in FIGS. 11A-11C utilize the capacitive coupling between the elongated conductive member 600 and the power and data coupling device 630. As such, the describes sensors can be provided power and can communicate data to an external device 110 without requiring a physical connection between the power and data coupling device 630 and the elongated conductive member 600. The lack of such a physical connection provides significant technical benefits to a user. For example, the user is no longer constrained by the presence of physical cords connecting to the elongated conductive member 600. Additionally, in the case of a guidewire system, for example, the user can feed medical devices, such as stents and catheters, over the wire 102 without having to remove or power down the wire 102. Such an ability allows the user to maintain uninterrupted sensor data from within the patient while placing the medical device onto the wire 102 and while placing the medical device within the human body.

Figure 12:
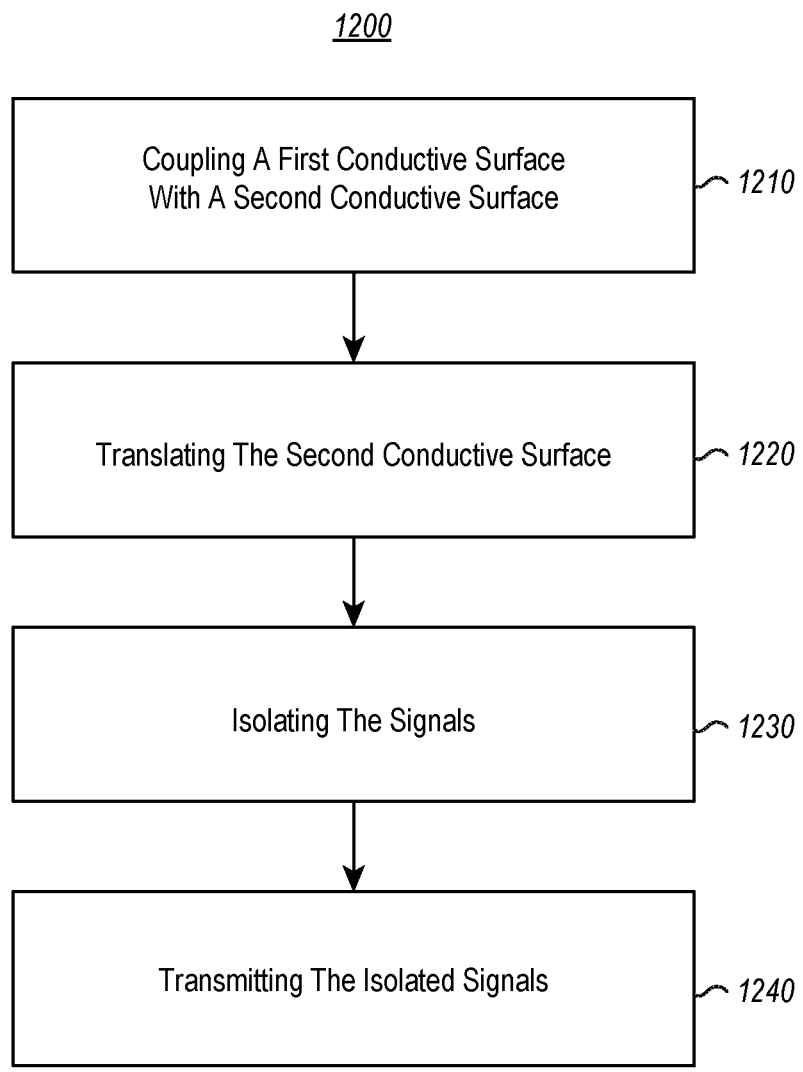
FIG. 12 illustrates a flow chart of a method for concurrent power and data transfer in a medical device.

FIG. 12 illustrates a flow chart of a method 1200 for providing power and data coupling to medical sensors. Method 1200 includes an act 1210 of coupling a first conductive surface with a second conductive surface. Act 1210 comprises coupling, via a time-varying electric field, a first conductive surface integrated into a medical device with a second conductive surface. The first conductive surface is connected to a power source for providing power to the second conductive surface, and the first conductive surface radiates a time-varying electric field that is configured to convey power to the second conductive surface. Additionally, the first conductive surface is configured to receive signals from the second conductive surface.

For example, as depicted and described with respect FIGS. 1, 2, and 8A-8D, the power and data coupling device 104 comprises a first conductive surface 800a. The first conductive surface 800a is connected to a power source (e.g., battery 810). The power source causes the first conductive surface 800a to radiate an electric field that couples with a second conductive surface 830, 840 and provides power to one or more sensors 121 ("medical sensors") that are coupled to the second conductive surface 830, 840. Additionally, as shown and described with respect to FIGS. 6A and 6B, the first conductive surface 800a is configured to receive signals (i.e., data signals) from the second conductive surface.

Method 1200 also includes an act 1220 of translating the second conductive surface. Act 1220 comprises translating the second conductive surface with respect to the first conductive surface. For example, as depicted and described with respect to FIGS. 1-3A, an elongated conductive member (i.e., the second conductive surface), such as a wire 102 or a catheter 202, can be translated through the power and data coupling device 104. The ability to translate the wire 102, the catheter 202, or some other medical device with respect to the first conductive surface allows a user to position the medical device within a luminal space for a medical procedure.

Additionally, method 1200 includes an act 1230 of isolating the signals. Act 1230 comprises isolating, with a signal processor, the signals. For example as depicted and described with respect to 6A and 6B, the power and data coupling device 630 comprises filters that are configured to isolate the data signals from each other.

Further, method 1200 includes an act 1240 of transmitting the isolated signals. Act 1240 comprises transmitting, with a transmitter, the isolated signals to a computing device. For example, as depicted and described with respect to FIGS. 6A, and 6B, a transmitter 640 can communicate the signals to an external device 110.

Aspects of the Invention

The invention is further specified in the following clauses:

Clause 1: A power and data coupling device for medical sensors comprising:

a first conductive surface integrated into a medical device and configured to couple via an electric field with a second conductive surface, the second conductive surface being translatable with respect to the first conductive surface, wherein:

the first conductive surface is connected to a power source for providing power, through the electric field, to the second conductive surface, the first conductive surface radiates a time-varying electric field that is configured to convey power to the second conductive surface, and the first conductive surface is connected to a pick-up that is configured to receive signals from the second conductive surface.

Clause 2: The power and data coupling device as recited in any preceding clause, further comprising: a signal collector configured to isolate the signals.

Clause 3: The power and data coupling device as recited in any preceding clause, further comprising: a transmitter configured to transmit the isolated signals to a computing device.

Clause 4: The power and data coupling device as recited in any preceding clause further comprising: one or more processors configured to process the signals.

Clause 5: The power and data coupling device as recited in any preceding clause, wherein at least a portion of the second conductive surface is encompassed by the first conductive surface.

Clause 6: The power and data coupling device as recited in any preceding clause, wherein the first conductive surface is not in physical contact with the second conductive surface.

Clause 7: The power and data coupling device as recited in any preceding clause, wherein the first conductive surface is in physical contact with the second conductive surface.

Clause 8: The power and data coupling device as recited in any preceding clause, further comprising an amplifier that is configured to amplify the signals.

Clause 9: The power and data coupling device as recited in any preceding clause, wherein the first conductive surface is configured to simultaneously (i) provide a power signal to the second conductive surface and (ii) receive a data signal from the second conductive surface.

Clause 10: The power and data coupling device as recited in any preceding clause, wherein the first conductive surface is configured to simultaneously (i) provide multiple, different power signals to the second conductive surface, each power signal in the multiple, different power signals is configured to provide power to a different set of medical sensors and (ii) receive multiple, different data signals from the second conductive surface, each data signal in the multiple, different data signals provides data from a different group of medical sensors.

Clause 11: The power and data coupling device as recited in any preceding clause, wherein the second conductive surface comprises a single conductive wire, the medical sensors being electrically coupled to the single conductive wire.

Clause 12: The power and data coupling device as recited in any preceding clause, wherein the first conductive surface comprises a portion of a catheter, the medical sensors being physically attached to the catheter.

Clause 13: The power and data coupling device as recited in any preceding clause, wherein the first conductive surface comprises a plurality of physically separate conductive surfaces.

Clause 14: The power and data coupling device as recited in any preceding clause, wherein each conductive surface selected from the plurality of physically separate conductive surfaces is configured to receive a data signal from a particular, different set of medical sensors.

Clause 15: The power and data coupling device as recited in any preceding clause, wherein a first conductive surface selected from the plurality of physically separate conductive surfaces is configured to provide power to at least one medical sensor and a second conductive surface selected from the plurality of physically separate conductive surfaces is configured to receive a data signal from the at least one medical sensor.

Clause 16: The power and data coupling device as recited in any preceding clause, wherein a power input line is physically connected to a feed on the first conductive surface, the feed being sized to substantially match an impedance of a coupling between the first conductive surface and the second conductive surface.

Clause 17: A method for providing power and data coupling to medical sensors comprising:

coupling, via a time-varying electric field, a first conductive surface integrated into a medical device with a second conductive surface, wherein:

the first conductive surface is connected to a power source for providing power to the second conductive surface, the first conductive surface radiates a time-varying electric field that is configured to convey power to the second conductive surface, and the first conductive surface is configured to receive signals from the second conductive surface;

translating the second conductive surface with respect to the first conductive surface;

isolating, with a signal processor, the signals; and transmitting, with a transmitter, the isolated signals to a computing device.

Clause 18: The method as recited in any preceding clause, wherein at least a portion of the second conductive surface is encompassed by the first conductive surface.

Clause 19: The method as recited in any preceding clause, wherein the first conductive surface is not in physical contact with the second conductive surface.

Clause 20: The method as recited in any preceding clause, further comprising:

translating a second elongated conductive member over or adjacent to the second conductive surface; and continue receiving the signals while the second elongated conductive member is positioned between the first conductive surface and the second conductive surface.

Clause 21: The method as recited in any preceding clause, wherein the first conductive surface is in physical contact with the second conductive surface.

Clause 22: The method as recited in any preceding clause, further comprising amplifying, with an amplifier, the signals.

Clause 23: The method as recited in any preceding clause further comprising simultaneously (i) providing a power signal to the second conductive surface and (ii) receiving a data signal from the second conductive surface.

Clause 24: The method as recited in any preceding clause, further comprising:

simultaneously (i) providing multiple, different power signals to the second conductive surface, each power signal in the multiple, different power signals is configured to provide power to a different set of medical sensors and (ii) receiving multiple, different data signals from the second conductive surface, each data signal in the multiple, different data signals provides data from a different group of medical sensors.

Clause 25: The method as recited in any preceding clause, wherein the first conductive surface comprises a single conductive wire, the medical sensors being electrically coupled to the single conductive wire.

Clause 26: The method as recited in any preceding clause, wherein the first conductive surface comprises a portion of a catheter, the medical sensors being physically attached to the catheter.

Clause 27: The method as recited in any preceding clause, wherein the first conductive surface comprises a plurality of physically separate conductive surfaces.

Clause 28: The method as recited in any preceding clause, further wherein multiple conductive surfaces selected from the plurality of physically separate conductive surfaces is configured to receive a data signal from a particular, different set of medical sensors.

Clause 29: The method as recited in any preceding clause, wherein a first conductive surface selected from the plurality of physically separate conductive surfaces is configured to provide power to at least one medical sensor and a second conductive surface selected from the plurality of physically separate conductive surfaces is configured to receive a data signal from the at least one medical sensor.

Clause 30: The method as recited in any preceding clause, wherein a power input line is physically connected to a feed on the first conductive surface, the feed being sized to substantially match an impedance of a coupling between the first conductive surface and the second conductive surface.

CONCLUSION

While certain embodiments of the present disclosure have been described in detail, with reference to specific configurations, parameters, components, elements, etcetera, the descriptions are illustrative and are not to be construed as limiting the scope of the claimed invention.

Furthermore, it should be understood that for any given element of component of a described embodiment, any of the possible alternatives listed for that element or component may generally be used individually or in combination with one another, unless implicitly or explicitly stated otherwise.

In addition, unless otherwise indicated, numbers expressing quantities, constituents, distances, or other measurements used in the specification and claims are to be understood as optionally being modified by the term "about" or its synonyms. When the terms "about," "approximately," "substantially," or the like are used in conjunction with a stated amount, value, or condition, it may be taken to mean an amount, value or condition that deviates by less than 20%, less than 10%, less than 5%, or less than 1% of the stated amount, value, or condition. At the very least, and not as an attempt to limit the application of the doctrine of equivalents to the scope of the claims, each numerical parameter should be construed in light of the number of reported significant digits and by applying ordinary rounding techniques.

Any headings and subheadings used herein are for organizational purposes only and are not meant to be used to limit the scope of the description or the claims.

It will also be noted that, as used in this specification and the appended claims, the singular forms "a," "an" and "the" do not exclude plural referents unless the context clearly dictates otherwise. Thus, for example, an embodiment referencing a singular referent (e.g., "widget") may also include two or more such referents.

It will also be appreciated that embodiments described herein may include properties, features (e.g., ingredients, components, members, elements, parts, and/or portions) described in other embodiments described herein. Accordingly, the various features of a given embodiment can be combined with and/or incorporated into other embodiments of the present disclosure. Thus, disclosure of certain features relative to a specific embodiment of the present disclosure should not be construed as limiting application or inclusion of said features to the specific embodiment. Rather, it will be appreciated that other embodiments can also include such features.

Further, the methods may be practiced by a computer system including one or more processors and computer-readable media such as computer memory. In particular, the computer memory may store computer-executable instructions that when executed by one or more processors cause various functions to be performed, such as the acts recited in the embodiments.

Computing system functionality can be enhanced by a computing systems' ability to be interconnected to other computing systems via network connections. Network connections may include, but are not limited to, connections via wired or wireless Ethernet, cellular connections, or even computer to computer connections through serial, parallel, USB, or other connections. The connections allow a computing system to access services at other computing systems and to quickly and efficiently receive application data from other computing systems.

Interconnection of computing systems has facilitated distributed computing systems, such as so-called "cloud" computing systems. In this description, "cloud computing" may be systems or resources for enabling ubiquitous, convenient, on-demand network access to a shared pool of configurable computing resources (e.g., networks, servers, storage, applications, services, etc.) that can be provisioned and released with reduced management effort or service provider interaction. A cloud model can be composed of various characteristics (e.g., on-demand self-service, broad network access, resource pooling, rapid elasticity, measured service, etc.), service models (e.g., Software as a Service ("SaaS"), Platform as a Service ("PaaS"), Infrastructure as a Service ("IaaS"), and deployment models (e.g., private cloud, community cloud, public cloud, hybrid cloud, etc.).

Cloud and remote based service applications are prevalent. Such applications are hosted on public and private remote systems such as clouds and usually offer a set of web-based services for communicating back and forth with clients.

Many computers are intended to be used by direct user interaction with the computer. As such, computers have input hardware and software user interfaces to facilitate user interaction. For example, a modern general-purpose computer may include a keyboard, mouse, touchpad, camera, etc. for allowing a user to input data into the computer. In addition, various software user interfaces may be available.

Examples of software user interfaces include graphical user interfaces, text command line-based user interface, function key or hot key user interfaces, and the like.

Disclosed embodiments may comprise or utilize a special purpose or general-purpose computer including computer hardware, as discussed in greater detail below. Disclosed embodiments also include physical and other computer-readable media for carrying or storing computer-executable instructions and/or data structures. Such computer-readable media can be any available media that can be accessed by a general purpose or special purpose computer system. Computer-readable media that store computer-executable instructions are physical storage media. Computer-readable media that carry computer-executable instructions are transmission media. Thus, by way of example, and not limitation, embodiments of the invention can comprise at least two distinctly different kinds of computer-readable media: physical computer-readable storage media and transmission computer-readable media.

Physical computer-readable storage media includes RAM, ROM, EEPROM, CD-ROM or other optical disk storage (such as CDs, DVDs, etc.), magnetic disk storage or other magnetic storage devices, or any other medium which can be used to store desired program code means in the form of computer-executable instructions or data structures and which can be accessed by a general purpose or special purpose computer.

A "network" is defined as one or more data links that enable the transport of electronic data between computer systems and/or modules and/or other electronic devices. When information is transferred or provided over a network or another communications connection (either hardwired, wireless, or a combination of hardwired or wireless) to a computer, the computer properly views the connection as a transmission medium. Transmission media can include a network and/or data links which can be used to carry program code in the form of computer-executable instructions or data structures and which can be accessed by a general purpose or special purpose computer. Combinations of the above are also included within the scope of computer-readable media.

Further, upon reaching various computer system components, program code means in the form of computer-executable instructions or data structures can be transferred automatically from transmission computer-readable media to physical computer-readable storage media (or vice versa). For example, computer-executable instructions or data structures received over a network or data link can be buffered in RAM within a network interface module (e.g., a "NIC"), and then eventually transferred to computer system RAM and/or to less volatile computer-readable physical storage media at a computer system. Thus, computer-readable physical storage media can be included in computer system components that also (or even primarily) utilize transmission media.

Computer-executable instructions comprise, for example, instructions and data which cause a general-purpose computer, special purpose computer, or special purpose processing device to perform a certain function or group of functions. The computer-executable instructions may be, for example, binaries, intermediate format instructions such as assembly language, or even source code. Although the subject matter has been described in language specific to structural features and/or methodological acts, it is to be understood that the subject matter defined in the appended claims is not necessarily limited to the described features or acts described above. Rather, the described features and acts are disclosed as example forms of implementing the claims.

Those skilled in the art will appreciate that the invention may be practiced in network computing environments with many types of computer system configurations, including, personal computers, desktop computers, laptop computers, message processors, hand-held devices, multi-processor systems, microprocessor-based or programmable consumer electronics, network PCs, minicomputers, mainframe computers, mobile telephones, PDAs, pagers, routers, switches, and the like. The invention may also be practiced in distributed system environments where local and remote computer systems, which are linked (either by hardwired data links, wireless data links, or by a combination of hardwired and wireless data links) through a network, both perform tasks. In a distributed system environment, program modules may be located in both local and remote memory storage devices.

Alternatively, or in addition, the functionality described herein can be performed, at least in part, by one or more hardware logic components. For example, and without limitation, illustrative types of hardware logic components that can be used include Field-programmable Gate Arrays (FPGAs), Program-specific Integrated Circuits (ASICs), Program-specific Standard Products (ASSPs), System-on-a-chip systems (SOCs), Complex Programmable Logic Devices (CPLDs), etc.

The present invention may be embodied in other specific forms without departing from its spirit or characteristics. The described embodiments are to be considered in all respects only as illustrative and not restrictive. The scope of the invention is, therefore, indicated by the appended claims rather than by the foregoing description. All changes which come within the meaning and range of equivalency of the claims are to be embraced within their scope.

What is claimed is:

1. A power and data coupling device for medical sensors comprising:
    a first conductive surface integrated into a medical device and configured to couple via an electric field with a second conductive surface, the medical device configured to remain outside a human body, the second conductive surface configured to be translatable with respect to the first conductive surface, wherein:
    the first conductive surface is connected to a power source for providing power, through the electric field, to the second conductive surface,
    the first conductive surface is configured to radiate a time-varying electric field that is configured to convey power to the second conductive surface, and
    the first conductive surface is connected to a pick-up that is configured to receive data signals from the second conductive surface, the data signals comprising data received from the medical sensors in electrical communication with the second conductive surface;
    wherein the first conductive surface is configured to simultaneously (i) provide multiple, different power signals to the second conductive surface, each power signal in the multiple, different power signals is configured to provide power to a different set of medical sensors and (ii) receive multiple, different data signals from the second conductive surface, each data signal in the multiple, different data signals provides data from a different group of medical sensors.

2. The power and data coupling device as recited in claim 1, further comprising:
    a signal collector configured to isolate the data signals.

3. The power and data coupling device as recited in claim 2, further comprising:
    a transmitter configured to transmit the isolated data signals to a computing device.

4. The power and data coupling device as recited in claim 1, further comprising:
    one or more processors configured to process the data signals.

5. The power and data coupling device as recited in claim 1, wherein at least a portion of the second conductive surface is encompassed by the first conductive surface.

6. The power and data coupling device as recited in claim 1, wherein the first conductive surface is not in physical contact with the second conductive surface.

7. The power and data coupling device as recited in claim 1, wherein the first conductive surface is in physical contact with the second conductive surface.

8. The power and data coupling device as recited in claim 1, further comprising an amplifier that is configured to amplify the data signals.

9. The power and data coupling device as recited in claim 1, wherein the second conductive surface comprises a single conductive wire, the medical sensors being electrically coupled to the single conductive wire.

10. The power and data coupling device as recited in claim 1, wherein the second conductive surface is in physical communication with a portion of a catheter, the medical sensors being physically attached to the catheter.

11. The power and data coupling device as recited in claim 1, wherein the first conductive surface comprises a plurality of physically separate conductive surfaces.

12. The power and data coupling device as recited in claim 11, wherein each conductive surface selected from the plurality of physically separate conductive surfaces is configured to receive a data signal from a particular, different set of medical sensors.

13. The power and data coupling device as recited in claim 11, wherein a particular conductive surface selected from the plurality of physically separate conductive surfaces is configured to provide power to at least one medical sensor and another conductive surface selected from the plurality of physically separate conductive surfaces is configured to receive a data signal from the at least one medical sensor.

14. The power and data coupling device as recited in claim 1, wherein a power input line is physically connected to a feed on the first conductive surface, the feed being sized to substantially match an impedance of a coupling between the first conductive surface and the second conductive surface.

15. A method for providing power and data coupling to medical sensors comprising:
coupling, via a time-varying electric field, a first conductive surface integrated into a medical device with a conductive guidewire, the medical device configured to remain outside a human body, wherein:
the first conductive surface is connected to a power source for providing power to the conductive guidewire,
the first conductive surface is configured to radiate a time-varying electric field that is configured to convey power to the conductive guidewire, and
the first conductive surface is configured to receive data signals from the conductive guidewire, the data signals comprising data received from the medical sensors in electrical communication with the conductive guidewire;
translating the conductive guidewire with respect to the first conductive surface;
simultaneously (i) providing multiple, different power signals to the conductive guidewire, each power signal in the multiple, different power signals is configured to provide power to a different set of the medical sensors and (ii) receiving multiple, different data signals from the conductive guidewire, each data signal in the multiple, different data signals provides data from a different group of the medical sensors;
isolating, with a signal processor, the data signals; and
transmitting, with a transmitter, the isolated data signals to a computing device.

16. The method as recited in claim 15, wherein at least a portion of the conductive guidewire is encompassed by the first conductive surface.

17. The method as recited in claim 15, wherein the first conductive surface is not in physical contact with the conductive guidewire.

18. The method as recited in claim 17, further comprising:
translating a second elongated conductive member over or adjacent to the conductive guidewire; and
continue receiving the data signals and transmitting power while the second elongated conductive member is positioned between the first conductive surface and the conductive guidewire.

19. The method as recited in claim 15, wherein the first conductive surface is in physical contact with the conductive guidewire.

20. The method as recited in claim 15, further comprising amplifying, with an amplifier, the data signals.

21. The method as recited in claim 15, wherein the first conductive surface comprises a single conductive wire, the medical sensors being electrically coupled to the single conductive wire.

22. The method as recited in claim 15, wherein the first conductive surface comprises a portion of a catheter, the medical sensors being physically attached to the catheter.

23. The method as recited in claim 15, wherein the first conductive surface comprises a plurality of physically separate conductive surfaces.

24. The method as recited in claim 23, wherein multiple conductive surfaces selected from the plurality of physically separate conductive surfaces are configured to receive a data signal from a particular, different set of the medical sensors.

25. The method as recited in claim 23, wherein a particular conductive surface selected from the plurality of physically separate conductive surfaces is configured to provide power to at least one medical sensor and another conductive surface selected from the plurality of physically separate conductive surfaces is configured to receive a data signal from the at least one medical sensor.

26. The method as recited in claim 15, wherein a power input line is physically connected to a feed on the first conductive surface, the feed being sized to substantially match an impedance of a coupling between the first conductive surface and the conductive guidewire.

\* \* \* \* \*